United States Patent
Itoi

(10) Patent No.: US 10,818,847 B2
(45) Date of Patent: Oct. 27, 2020

(54) COMPOUND INCLUDING NITROGEN AND ORGANIC ELECTROLUMINESCENCE DEVICE INCLUDING THE SAME

(71) Applicant: Samsung Display Co., Ltd., Yongin-si, Gyeonggi-do (KR)

(72) Inventor: Hiroaki Itoi, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 346 days.

(21) Appl. No.: 15/975,077

(22) Filed: May 9, 2018

(65) Prior Publication Data

US 2019/0131536 A1    May 2, 2019

(30) Foreign Application Priority Data

Oct. 27, 2017   (KR) .................. 10-2017-0141538

(51) Int. Cl.
  *C07D 403/10*    (2006.01)
  *C07D 403/14*    (2006.01)
  (Continued)

(52) U.S. Cl.
  CPC ........ *H01L 51/0067* (2013.01); *C07D 403/14* (2013.01); *C07D 405/14* (2013.01);
  (Continued)

(58) Field of Classification Search
  CPC .. C07D 403/10; C07D 403/14; C07D 209/82; H01L 51/0067; H01L 51/0072
  See application file for complete search history.

(56) References Cited

U.S. PATENT DOCUMENTS 8,227,798 B2    7/2012  Kai et al.
2007/0257600 A1   11/2007  Matsuura et al.
(Continued)

FOREIGN PATENT DOCUMENTS

EP    3275968 A1    1/2018
JP    5179720 B2    1/2013
(Continued)

OTHER PUBLICATIONS

SciFinder Search (Jun. 10, 2020).*
EPO Extended Search Report dated Dec. 6, 2018, for corresponding European Patent Application No. 18202173.3 (5 pages).

*Primary Examiner* — Vu A Nguyen
(74) *Attorney, Agent, or Firm* — Lewis Roca Rothgerber Christie LLP

(57) ABSTRACT

A compound including nitrogen, represented by Formula 1, and an organic electroluminescence device including the same are provided:

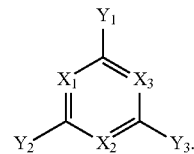

Formula 1

In Formula 1, $X_1$ to $X_3$ may each independently be CR or N, at least two of $X_1$ to $X_3$ may be N, $Y_1$ to $Y_3$ may each independently be represented by one of Formulae 2 to 4, and at least two of $Y_1$ to $Y_3$ may be represented by Formula 3 or 4:

(Continued)

Formula 2

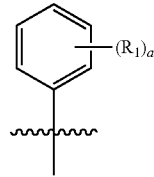

Formula 3

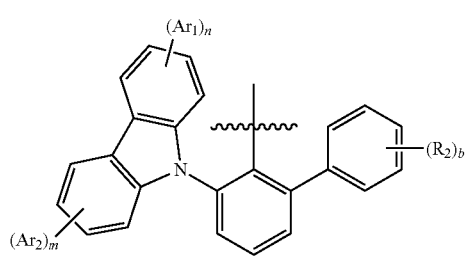

Formula 4

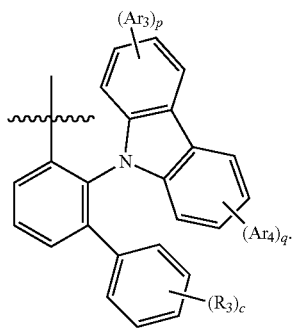

20 Claims, 2 Drawing Sheets

(51) Int. Cl.
  *H01L 51/00* (2006.01)
  *H01L 51/50* (2006.01)
  *C09K 11/06* (2006.01)
  *C07D 409/14* (2006.01)
  *C07D 405/14* (2006.01)

(52) U.S. Cl.
  CPC ............ *C07D 409/14* (2013.01); *C09K 11/06* (2013.01); *H01L 51/0032* (2013.01); *H01L 51/0072* (2013.01); *C09K 2211/1018* (2013.01); *H01L 51/5012* (2013.01); *H01L 51/5016* (2013.01); *H01L 51/5024* (2013.01); *H01L 51/5056* (2013.01); *H01L 51/5072* (2013.01); *H01L 51/5088* (2013.01); *H01L 51/5092* (2013.01); *H01L 51/5096* (2013.01)

(56) References Cited

U.S. PATENT DOCUMENTS

2015/0228908 A1    8/2015    Lee et al.
2016/0013423 A1    1/2016    Huh et al.

FOREIGN PATENT DOCUMENTS

| | | |
|---|---|---|
| JP | 2014-503502 A | 2/2014 |
| JP | 2016-17078 A | 2/2016 |
| KR | 10-1159373 B1 | 6/2012 |
| KR | 10-1474232 B1 | 12/2014 |
| KR | 10-2015-0094398 A | 8/2015 |
| KR | 10-2016-0006629 A | 1/2016 |
| KR | 10-2016-0116297 A | 10/2016 |
| WO | WO 2012/069121 A1 | 5/2012 |
| WO | WO 2014/092083 A1 | 6/2014 |
| WO | WO 2016/158540 A1 | 10/2016 |
| WO | WO 2016/159479 A1 | 10/2016 |
| WO | WO-2016159479 A1 * | 10/2016 ........... C07D 403/10 |
| WO | WO 2016/181846 A1 | 11/2016 |

\* cited by examiner

COMPOUND INCLUDING NITROGEN AND ORGANIC ELECTROLUMINESCENCE DEVICE INCLUDING THE SAME

CROSS-REFERENCE TO RELATED APPLICATION

This application claims priority to and the benefit of Korean Patent Application No. 10-2017-0141538, filed on Oct. 27, 2017, the entire content of which is hereby incorporated by reference.

BACKGROUND

Aspects of embodiments of the present disclosure relate to a compound including nitrogen, and an organic electroluminescence device including the same.

Development of organic electroluminescence-based image displays is being actively conducted. Organic electroluminescence displays differ from liquid crystal displays in that they are so called self-luminescent displays, which function via the recombination of holes and electrons injected from a first electrode and a second electrode, respectively, into an emission layer, resulting in light emission from a luminescent organic compound in the emission layer.

Organic electroluminescence devices including, for example, a first electrode, a hole transport layer on the first electrode, an emission layer on the hole transport layer, an electron transport layer on the emission layer, and a second electrode on the electron transport layer are available in the art. Holes are injected into the device by the first electrode, and the injected holes move through the hole transport layer and are injected into the emission layer. Meanwhile, electrons are injected into the device by the second electrode, and the injected electrons move through the electron transport layer and are injected into the emission layer. The holes and electrons injected into the emission layer recombine to produce excitons in the emission layer. The organic electroluminescence device emits light generated by the transition of the excitons to the ground state.

SUMMARY

Aspects of embodiments of the present disclosure provide a compound including nitrogen, and an organic electroluminescence device including the same.

Aspects of embodiments of the present disclosure provide a compound including nitrogen, represented by Formula 1:

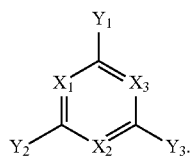

Formula 1

In Formula 1, $X_1$ to $X_3$ may each independently be CR or N; at least two of $X_1$ to $X_3$ may be N; R may be a hydrogen atom, a deuterium atom, or a substituted or unsubstituted alkyl group having 1 to 10 carbon atoms; $Y_1$ to $Y_3$ may each independently be represented by one of Formulae 2 to 4; and at least two of $Y_1$ to $Y_3$ may be represented by Formula 3 or 4:

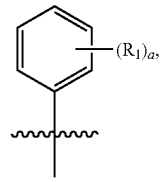

Formula 2

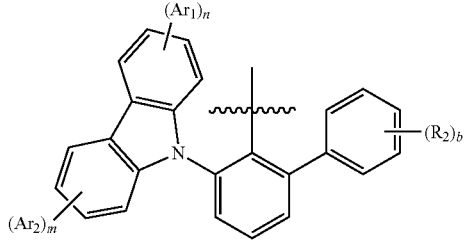

Formula 3

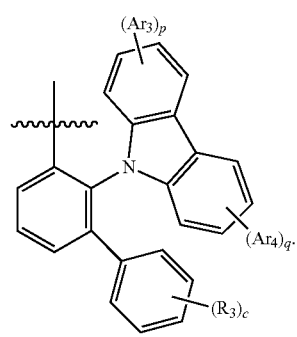

Formula 4

In Formulae 2 to 4, $R_1$ to $R_3$ may each independently be a hydrogen atom, a deuterium atom, a halogen atom, a substituted or unsubstituted alkyl group having 1 to 10 carbon atoms, or a substituted or unsubstituted aryl group having 6 to 30 carbon atoms for forming a ring; $Ar_1$ to $Ar_4$ may each independently be a hydrogen atom, a deuterium atom, a halogen atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring; "a" to "c" may each independently be an integer of 0 to 5; and "n", "m", "p", and "q" may each independently be an integer of 0 to 4.

In some embodiments, $R_1$ to $R_3$ may each independently be a hydrogen atom, a deuterium atom, a fluorine atom, a substituted or unsubstituted alkyl group having 1 to 4 carbon atoms, a substituted or unsubstituted phenyl group, or a substituted or unsubstituted biphenyl group.

In some embodiments, $Ar_1$ to $Ar_4$ may each independently be a hydrogen atom, a deuterium atom, a fluorine atom, a substituted or unsubstituted alkyl group having 1 to 4 carbon atoms, a substituted or unsubstituted phenyl group, a substituted or unsubstituted biphenyl group, a substituted or unsubstituted carbazole group, a substituted or unsubstituted dibenzofuran group, or a substituted or unsubstituted dibenzothiophene group.

In some embodiments, two of $X_1$ to $X_3$ may be N, and the remaining one may be CH.

In some embodiments, all $X_1$ to $X_3$ may be N.

In some embodiments, $Y_1$ to $Y_3$ may each independently be represented by Formula 3 or 4.

In some embodiments, the absolute value of a difference between a singlet energy level of the compound and a triplet energy level of the compound may be about 0.2 eV or less.

According to one or more embodiments of the present disclosure, an organic electroluminescence device includes a first electrode, a hole transport region on the first electrode, an emission layer on the hole transport region, an electron transport region on the emission layer, and a second electrode on the electron transport region, wherein the emission layer includes the compound including nitrogen according to an embodiment of the present disclosure.

In an embodiment, the first electrode and the second electrode may each independently include at least one selected from Ag, Mg, Cu, Al, Pt, Pd, Au, Ni, Nd, Ir, Cr, Li, Ca, LiF/Ca, LiF/Al, Mo, Ti, In, Sn, and Zn, a compound of two or more thereof, a mixture of two or more thereof, or an oxide thereof.

In some embodiments, the emission layer may include a host and a dopant, and the dopant may include the compound including nitrogen according to an embodiment of the present disclosure.

In some embodiments, the dopant may include a first dopant and a second dopant, and the first dopant or the second dopant may include the compound including nitrogen according to an embodiment of the present disclosure.

In some embodiments, the emission layer may be to emit thermally activated delayed fluorescence.

BRIEF DESCRIPTION OF THE DRAWINGS

The accompanying drawings are included to enable further understanding of the present disclosure, and are incorporated in and constitute a part of this specification. The drawings illustrate example embodiments of the present disclosure and, together with the description, serve to explain principles of the present disclosure. In the drawings.

DETAILED DESCRIPTION

Figure 1:
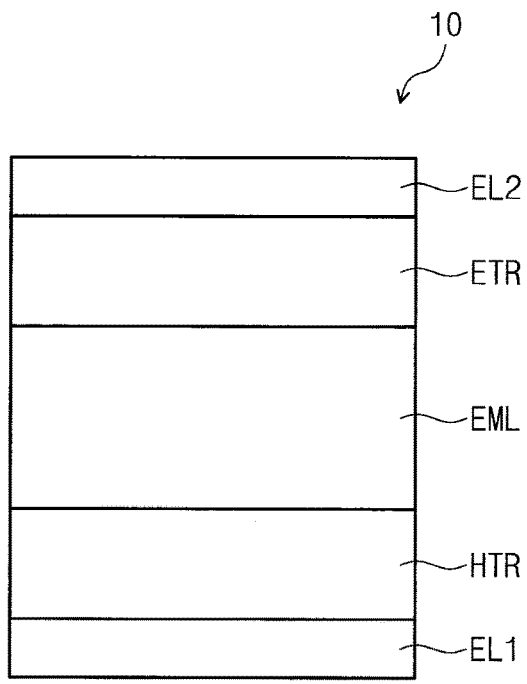
FIG. 1 is a cross-sectional view schematically illustrating an organic electroluminescence device according to an embodiment of the present disclosure.

The above objects, other objects, features, and advantages of the present disclosure will be described more fully hereinafter with reference to the accompanying drawings, in which example embodiments of the disclosure are shown. The present disclosure may, however, be embodied in different forms and should not be construed as being limited to the embodiments set forth herein. Rather, the example embodiments set forth herein are provided to sufficiently provide a person skilled in the art with the spirit of the present disclosure for thoroughness and completeness of the contents disclosed herein.

Like reference numerals refer to like elements within the drawings, and duplicative descriptions thereof may not be provided. In the drawings, the sizes of elements may be enlarged for clarity of the present disclosure. It will be understood that although the terms first, second, etc. may be used herein to describe various elements, the elements should not be limited by these terms. These terms are only used to distinguish one element from another element. For example, a first element could be alternatively termed a second element, and similarly, a second element could be alternatively termed a first element. As used herein, the singular forms are intended to include the plural forms as well, unless the context clearly indicates otherwise.

It will be further understood that the terms "comprises" or "comprising," when used in this specification, specify the presence of stated features, numerals, steps, operations, elements, parts, or a combination thereof, but do not preclude the presence or addition of one or more other features, numerals, steps, operations, elements, parts, or a combination thereof. It will also be understood that when a layer, a film, a region, a plate, etc. is referred to as being "on" another part, it may be "directly on" the other part, or intervening layers may also be present. On the contrary, when a layer, a film, a region, a plate, etc. is referred to as being "under" another part, it may be "directly under" the other part, or intervening layers may also be present.

In the present disclosure,

refers to a part to be connected (e.g., a connection point to another molecule, moiety, etc.,).

In the present disclosure, "substituted or unsubstituted" may refer to substitution with at least one substituent selected from the group consisting of a deuterium atom, a halogen atom, a cyano group, a nitro group, an amino group, a silyl group, a boron group, a phosphine group, an alkyl group, an alkenyl group, an aryl group, and a heterocyclic group, or the unsubstituted state (e.g., bearing only hydrogen atoms). In addition, each of the substituents illustrated above may themselves be substituted or unsubstituted. For example, a biphenyl group may be interpreted as an aryl group, as well as a phenyl group substituted with a phenyl group.

In the present disclosure, the term 'halogen atom' may include (e.g., be selected from) a fluorine atom, a chlorine atom, a bromine atom, and/or an iodine atom.

In the present disclosure, the term 'alkyl group' may refer to an alkyl group having a linear or branched chain or a cycle shape. The carbon number of the alkyl group may be 1 to 30, 1 to 20, 1 to 10, or 1 to 4. Non-limiting examples of the alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldodecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyl eicosyl, 2-butyl eicosyl, 2-hexyl eicosyl, 2-octyl eicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc.

In the present disclosure, the term 'aryl group' may refer to an optional functional group or substituent derived from an aromatic hydrocarbon ring. The aryl group may be a monocyclic aryl group or a polycyclic aryl group. The carbon number of the aryl group for forming a ring may be 6 to 30, 6 to 20, or 6 to 15. Non-limiting examples of the aryl group may include phenyl, naphthyl, fluorenyl, anthracenyl, phenanthryl, biphenyl, terphenyl, quaterphenyl, quinqphenyl, sexiphenyl, biphenylene, triphenylene, pyrenyl, benzofluoranthenyl, chrysenyl, etc.

In the present disclosure, a fluorenyl group may be substituted (e.g., at the 9-H position), and/or two substituents may be combined (e.g., linked) with each other to form a spiro structure. Non-limiting examples of the substituted fluorenyl group are shown below. However, embodiments of the present disclosure are not limited thereto:

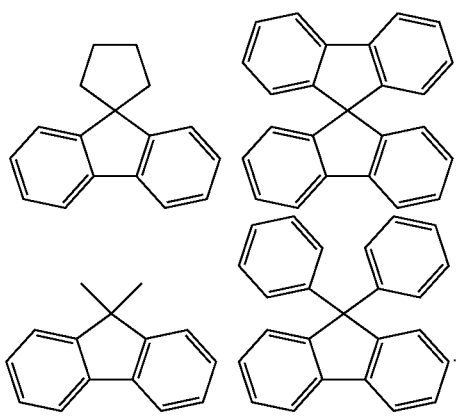

In the present disclosure, the heteroaryl group may be a heteroaryl group including at least one of O, N, P, Si or S as a heteroatom. When the heteroaryl group includes two heteroatoms, the two heteroatoms may be the same or different from each other. The carbon number of the heteroaryl group for forming a ring may be 2 to 30, or 2 to 20. The heteroaryl group may be a monocyclic heteroaryl group or a polycyclic heteroaryl group. The heteroaryl group may have a structure of, for example, two rings or three rings. Non-limiting examples of the heteroaryl group may include thiophene, furan, pyrrole, imidazole, thiazole, oxazole, oxadiazole, triazole, pyridine, bipyridine, pyrimidine, triazine, triazole, acridyl, pyridazine, pyrazinyl, quinoline, quinazoline, quinoxaline, phenoxazine, phthalazine, pyrido pyrimidine, pyrido pyrazine, pyrazino pyrazine, isoquinoline, indole, carbazole, N-arylcarbazole, N-heteroaryl carbazole, N-alkyl carbazole, benzoxazole, benzimidazole, benzothiazole, benzocarbazole, benzothiophene, dibenzothiophene, thienothiophene, benzofuran, phenanthroline, thiazole, isooxazole, oxadiazole, thiadiazole, phenothiazine, dibenzosilole, dibenzofuran, etc.

In the present disclosure, the term 'silyl group' may include alkylsilyl groups and arylsilyl groups. Non-limiting examples of the silyl group may include trimethylsilyl, triethylsilyl, t-butyldimethylsilyl, vinyldimethylsilyl, propyldimethylsilyl, triphenylsilyl, diphenylsilyl, phenylsilyl, etc.

In the present disclosure, the term 'boron group' may include alkyl boron groups and aryl boron groups. Non-limiting examples of the boron group may include trimethylboron, triethylboron, t-butyldimethyl boron, triphenylboron, diphenylboron, phenylboron, etc.

In the present disclosure, an alkenyl group may be linear or branched. The carbon number is not specifically limited, but may be 2 to 30, 2 to 20, or 2 to 10. Non-limiting examples of the alkenyl group may include vinyl, 1-butenyl, 1-pentenyl, 1,3-butadienyl aryl, styrenyl, styrylvinyl, etc.

In the present disclosure, the carbon number of the amino group is not specifically limited, but may be 1 to 30. The term 'amino group' may include alkylamino groups and arylamino groups. Non-limiting examples of the amino group may include a methylamino group, a dimethylamino group, a phenylamino group, a diphenylamino group, a naphthylamino group, a 9-methyl-anthracenylamino group, a triphenylamino group, etc.

First, the compound including nitrogen according to an embodiment of the present disclosure will be explained.

The compound including nitrogen according to an embodiment of the present disclosure may be represented by Formula 1:

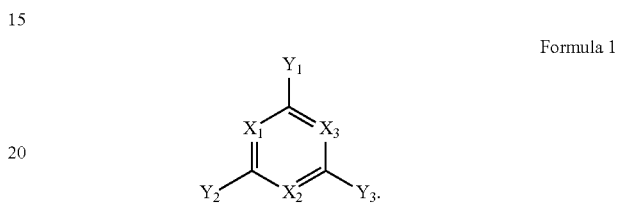

Formula 1

In Formula 1, $X_1$ to $X_3$ may each independently be CR or N; and R may be a hydrogen atom, a deuterium atom, or a substituted or unsubstituted alkyl group having 1 to 10 carbon atoms. At least two of $X_1$ to $X_3$ may be N.

In Formula 1, $Y_1$ to $Y_3$ may each independently be represented by one of Formulae 2 to 4, and at least two of $Y_1$ to $Y_3$ may be represented by Formula 3 or 4:

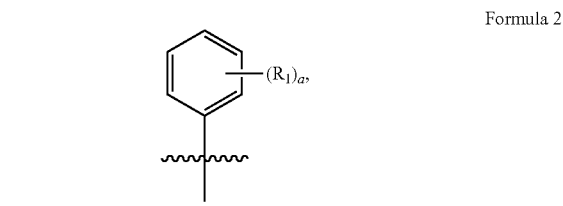

Formula 2

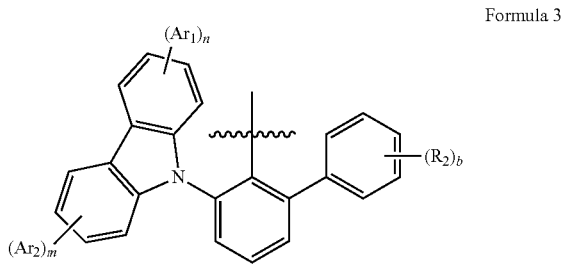

Formula 3

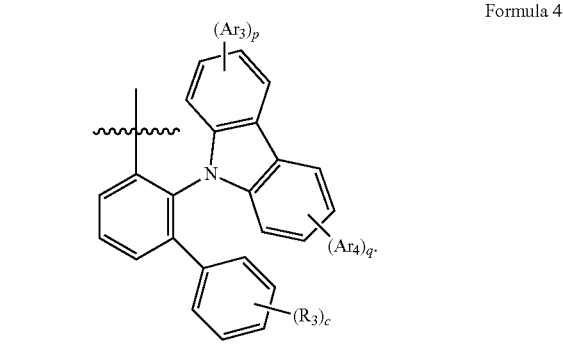

Formula 4

In Formula 2, $R_1$ may be a hydrogen atom, a deuterium atom, a halogen atom, a substituted or unsubstituted alkyl group having 1 to 10 carbon atoms, or a substituted or unsubstituted aryl group having 6 to 30 carbon atoms for forming a ring; and "a" may be an integer of 0 to 5.

When "a" is 2 or more, a plurality of $R_1$ groups may be the same or different, and when "a" is 1 or more, $R_1$ may not be a hydrogen atom.

In Formula 3, $R_2$ may be a hydrogen atom, a deuterium atom, a halogen atom, a substituted or unsubstituted alkyl group having 1 to 10 carbon atoms, or a substituted or unsubstituted aryl group having 6 to 30 carbon atoms for forming a ring; and "b" may be an integer of 0 to 5.

When "b" is 2 or more, a plurality of $R_2$ groups may be the same or different, and when "b" is 1 or more, $R_2$ may not be a hydrogen atom.

In Formula 3, $Ar_1$ and $Ar_2$ may each independently be a hydrogen atom, a deuterium atom, a halogen atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring; and "n" and "m" may each independently be an integer of 0 to 4.

When "n" is 2 or more, a plurality of $Ar_1$ groups may be the same or different, and when "n" is 1 or more, $Ar_1$ may not be a hydrogen atom. When "m" is 2 or more, a plurality of $Ar_2$ groups may be the same or different, and when "m" is 1 or more, $Ar_2$ may not be a hydrogen atom.

In Formula 4, $R_3$ may be a hydrogen atom, a deuterium atom, a halogen atom, a substituted or unsubstituted alkyl group having 1 to 10 carbon atoms, or a substituted or unsubstituted aryl group having 6 to 30 carbon atoms for forming a ring; and "c" may be an integer of 0 to 5.

When "c" is 2 or more, a plurality of $R_3$ groups may be the same or different, and when "c" is 1 or more, $R_3$ may not be a hydrogen atom.

In Formula 4, $Ar_3$ and $Ar_4$ may each independently be a hydrogen atom, a deuterium atom, a halogen atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring; and "p" and "q" may each independently be an integer of 0 to 4.

When "p" is 2 or more, a plurality of $Ar_3$ groups may be the same or different, and when "p" is 1 or more, $Ar_3$ may not be a hydrogen atom. When "q" is 2 or more, a plurality of $Ar_4$ groups may be the same or different, and when "q" is 1 or more, $Ar_4$ may not be a hydrogen atom.

In some embodiments, each of $R_1$ to $R_3$ may be a hydrogen atom. However, embodiments of the present disclosure are not limited thereto, and at least one of $R_1$ to $R_3$ may be a deuterium atom, a fluorine atom, a substituted or unsubstituted alkyl group having 1 to 4 carbon atoms, a substituted or unsubstituted phenyl group, or a substituted or unsubstituted biphenyl group.

In some embodiments, "a" may be 0. However, embodiments of the present disclosure are not limited thereto, and "a" may be 1 and $R_1$ may be a deuterium atom or a substituted or unsubstituted phenyl group.

In some embodiments, "b" may be 0. However, embodiments of the present disclosure are not limited thereto, and "b" may be 1 and $R_2$ may be a deuterium atom or a fluorine atom.

In some embodiments, "c" may be 0. However, embodiments of the present disclosure are not limited thereto, and "c" may be 1 and $R_3$ may be a deuterium atom or a fluorine atom.

In some embodiments, $Ar_1$ to $Ar_4$ may each independently be a hydrogen atom. However, embodiments of the present disclosure are not limited thereto, and at least one of $Ar_1$ to $Ar_4$ may be a deuterium atom, a fluorine atom, a substituted or unsubstituted alkyl group having 1 to 4 carbon atoms, a substituted or unsubstituted phenyl group, a substituted or unsubstituted biphenyl group, or a substituted or unsubstituted polycyclic heteroaryl group. At least one of $Ar_1$ to $Ar_4$ may be a deuterium atom, a fluorine atom, a methyl group, a t-butyl group, a substituted or unsubstituted phenyl group, a substituted or unsubstituted biphenyl group, a substituted or unsubstituted carbazole group, a substituted or unsubstituted dibenzofuran group, or a substituted or unsubstituted dibenzothiophene group.

In some embodiments, "n" and "m" may be 0. However, embodiments of the present disclosure are not limited thereto, and n+m may be 1 or 2. In this case, at least one of $Ar_1$ or $Ar_2$ may be a substituted or unsubstituted methyl group, a substituted or unsubstituted t-butyl group, a substituted or unsubstituted carbazole group, a substituted or unsubstituted dibenzothiophene group, or a substituted or unsubstituted dibenzofuran group. When "n" and "m" are each 1, for example, $Ar_1$ and $Ar_2$ may be the same. In some embodiments, at least one of "n" or "m" may be 2 or more.

In some embodiments, "p" and "q" may each be 0. In some embodiments, p+q may be 1 or 2. However, embodiments of the present disclosure are not limited thereto, and in some embodiments, at least one of "p" or "q" may be 2 or more. At least one of $Ar_3$ or $Ar_4$ may be a substituted or unsubstituted methyl group, a substituted or unsubstituted t-butyl group, a substituted or unsubstituted carbazole group, a substituted or unsubstituted dibenzothiophene group, or a substituted or unsubstituted dibenzofuran group. When "p" and "q" are each 1, for example, $Ar_3$ and $Ar_4$ may be the same.

In Formulae 3 and 4, the phenylene group that is connected with Formula 1 is not substituted with any substituents other than a substituted or unsubstituted phenyl group and a substituted or unsubstituted carbazole group. In Formulae 3 and 4, the substituted or unsubstituted phenyl group and the substituted or unsubstituted carbazole group may be substituted on the phenylene group that is connected with Formula 1, at specific positions.

In some embodiments, in Formula 1, $X_1$ to $X_3$ may all (each) be N. In this case, the compound including nitrogen according to an embodiment of the present disclosure may be a triazine-based compound.

In some embodiments, in Formula 1, two of $X_1$ to $X_3$ may be N, and the remaining one may be CR. In this case, the compound including nitrogen according to an embodiment of the present disclosure may be a pyrimidine-based compound. R may be the same as described above, for example, R may be a hydrogen atom.

Formula 1 may be, for example, represented by Formula 1-1:

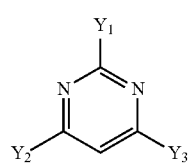

Formula 1-1

In Formula 1-1, $Y_1$ may be represented by one of Formulae 2 to 4, and $Y_2$ and $Y_3$ may each independently be represented by Formula 3 or 4.

Formula 1 may be, for example, represented by Formula 1-2:

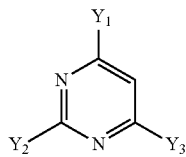

Formula 1-2

In Formula 1-2, $Y_1$ may be represented by one of Formulae 2 to 4, and $Y_2$ and $Y_3$ may each independently be represented by Formula 3 or 4.

Formula 1 may be, for example, represented by Formula 1-3:

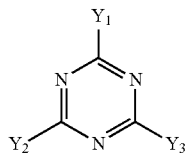

Formula 1-3

In Formula 1-3, $Y_1$ may be represented by one of Formulae 2 to 4, and $Y_2$ and $Y_3$ may each independently be represented by Formula 3 or 4. For example, $Y_1$ may be represented by Formula 2.

In Formula 1, $Y_1$ to $Y_3$ may each independently be represented by Formula 3 or 4. In this case, the compound including nitrogen according to an embodiment of the present disclosure may include three carbazole groups.

The compound including nitrogen that is represented by Formula 1 according to an embodiment of the present disclosure may be one selected from the compounds represented in Compound Group 1. However, embodiments of the present disclosure are not limited thereto.

Compound Group 1

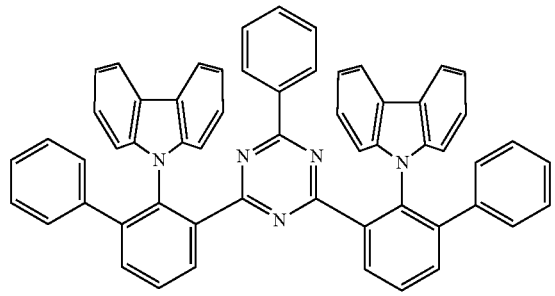

T-01

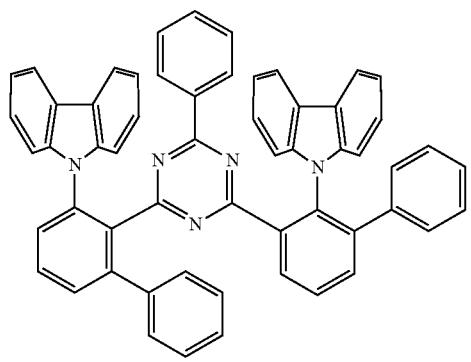

T-02

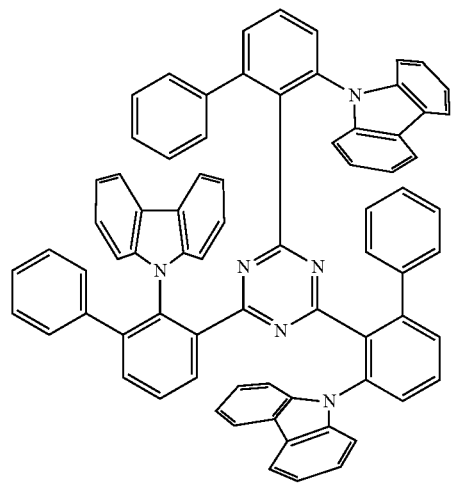

T-03

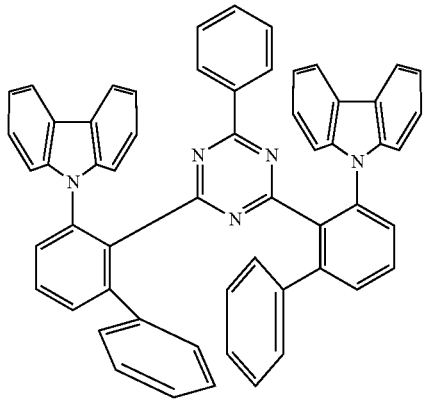

T-04

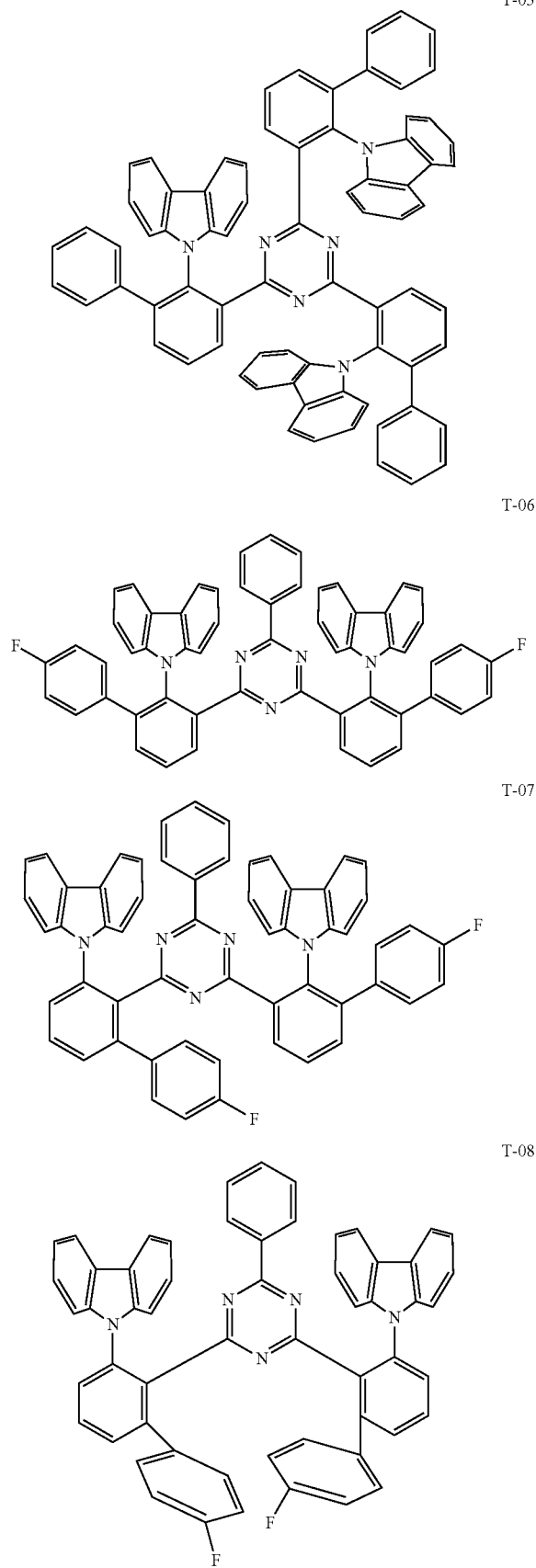
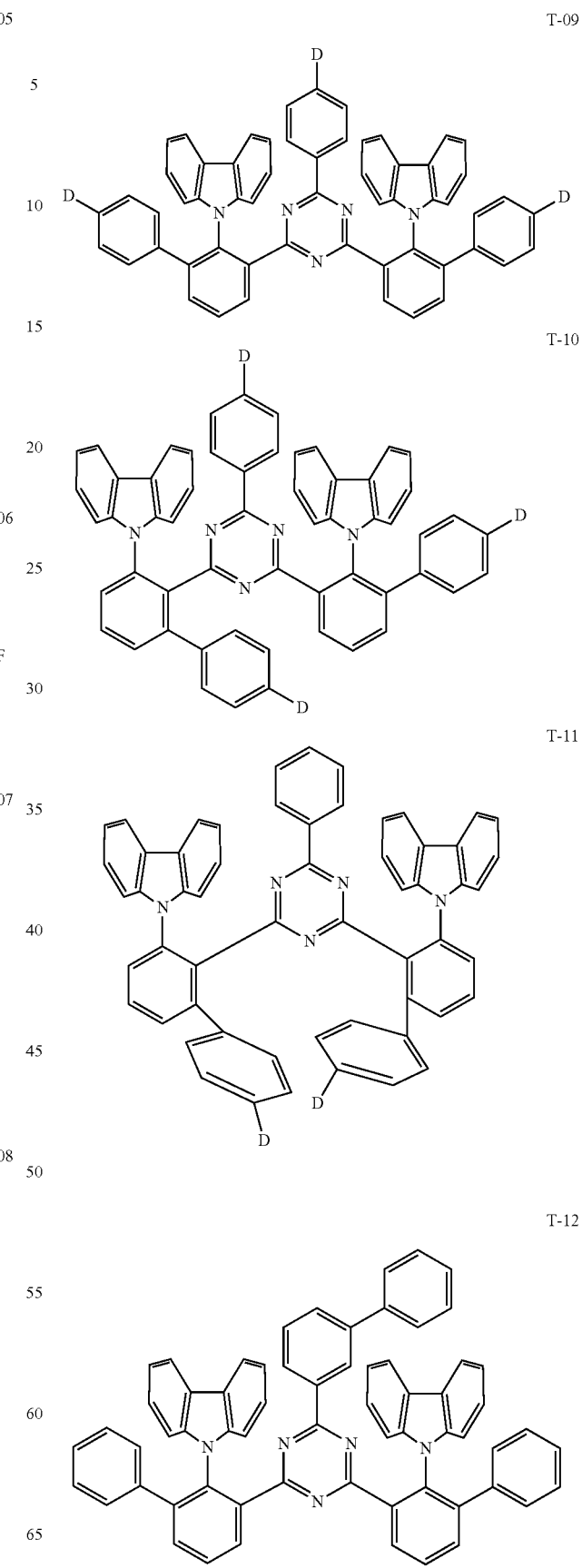

T-13
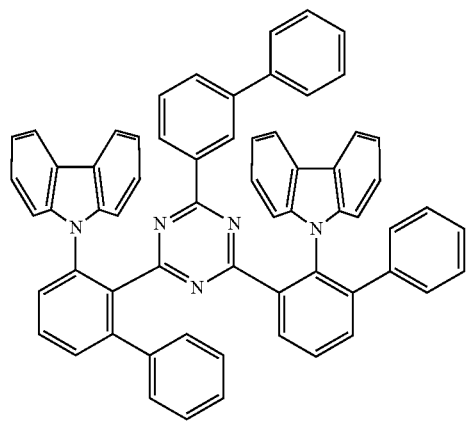
T-16
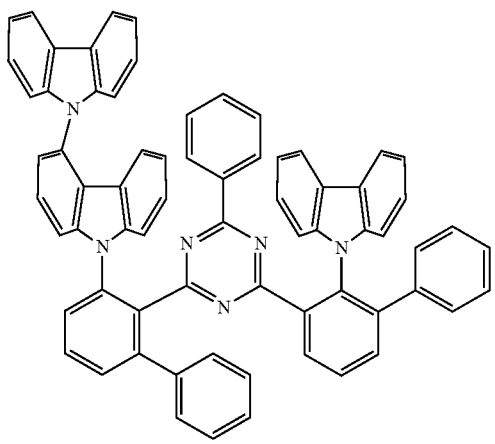
T-14
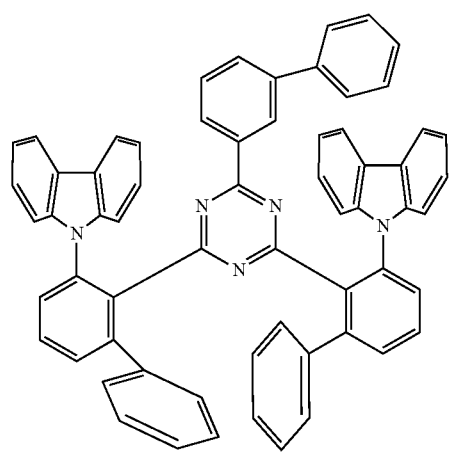
T-17
T-15
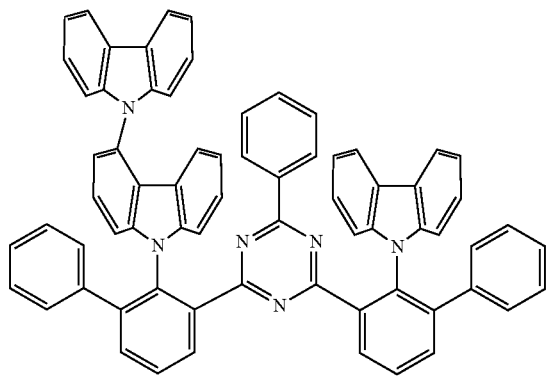
T-18
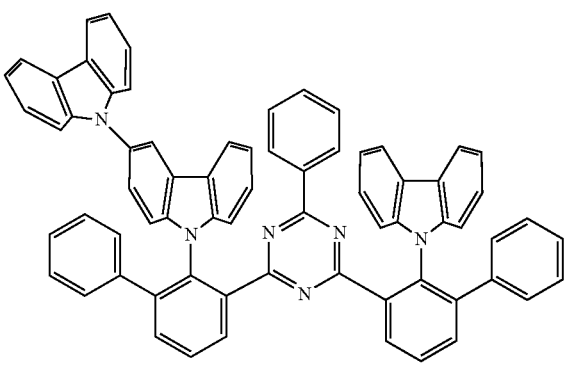

T-19
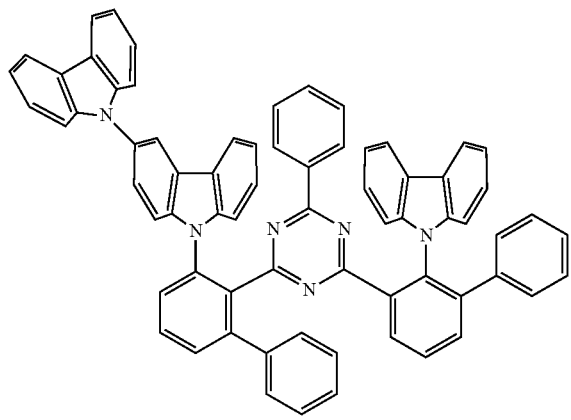
T-20
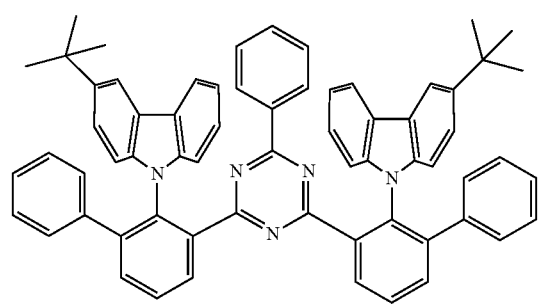
T-21
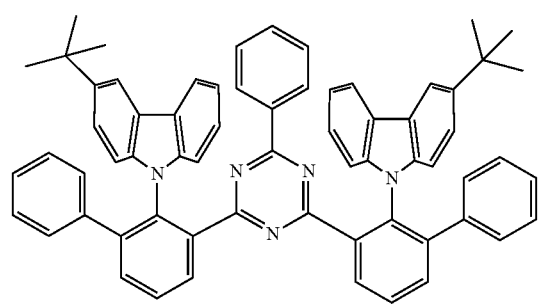
T-22
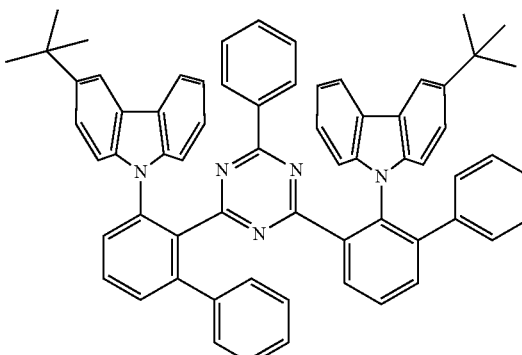
T-23
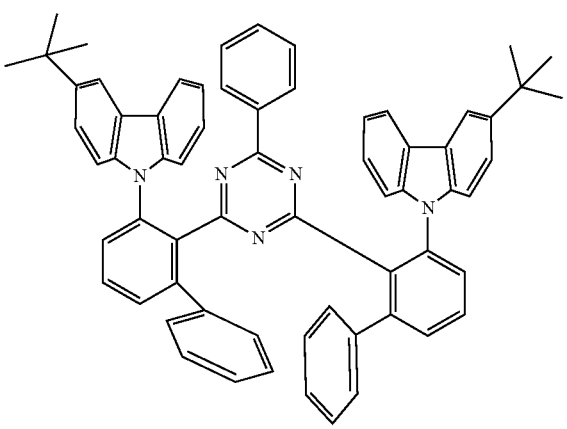
T-24
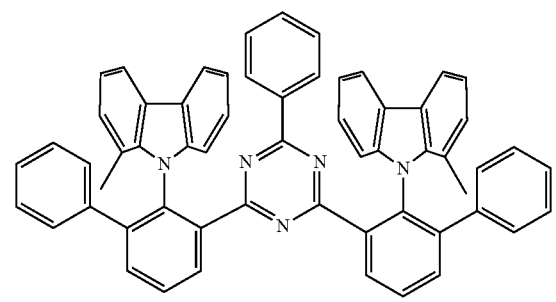
T-25
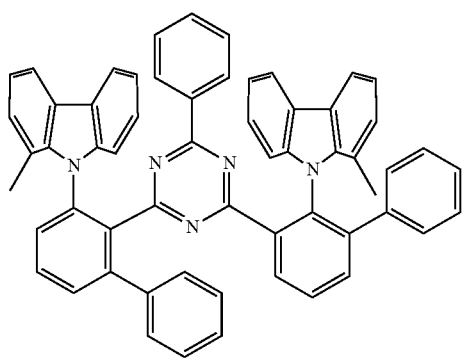

T-26
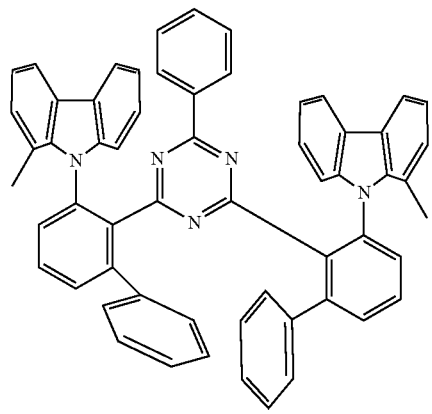
Compound Group 2
T-29
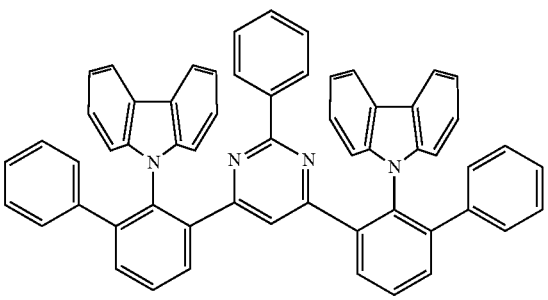
T-27
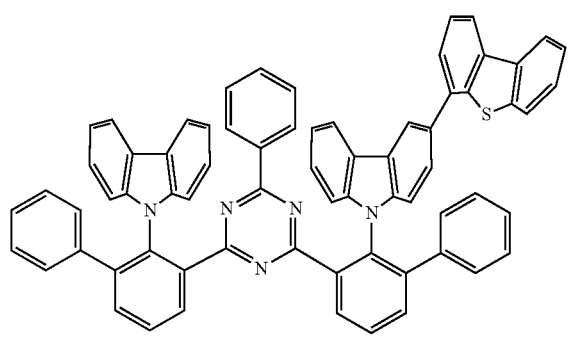
T-30
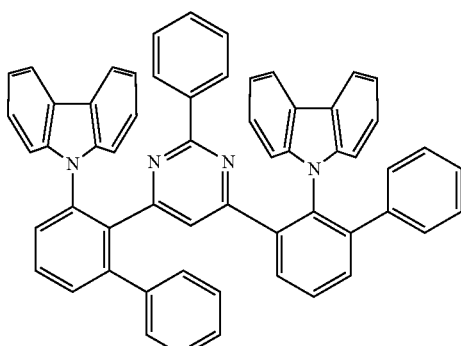
T-28
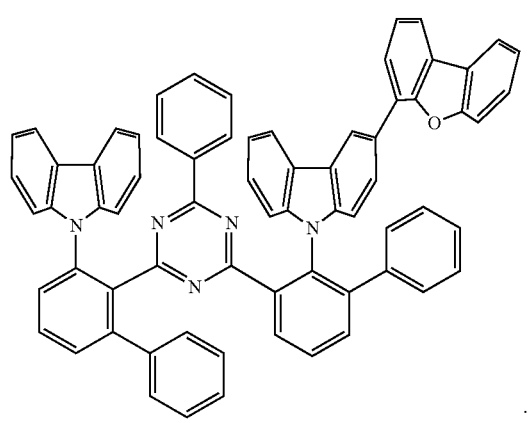
T-31
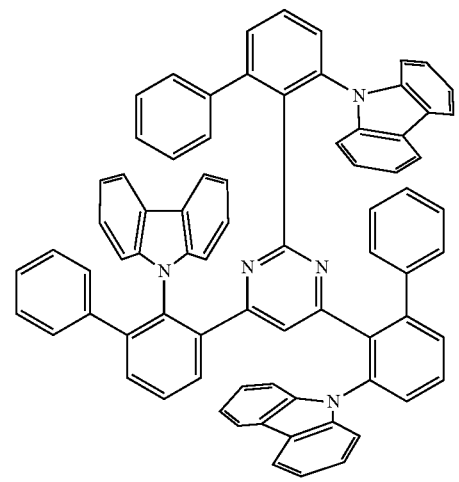
T-32
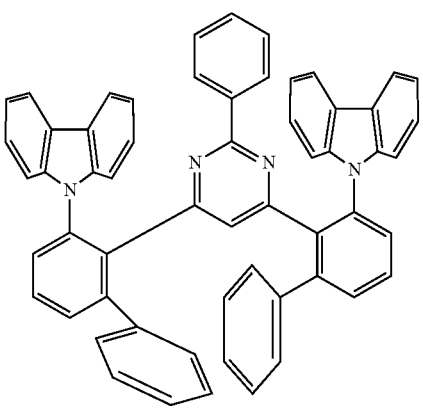
The compound including nitrogen that is represented by Formula 1 according to an embodiment of the present disclosure may be one selected from the compounds represented in Compound Group 2. However, embodiments of the present disclosure are not limited thereto.

T-33
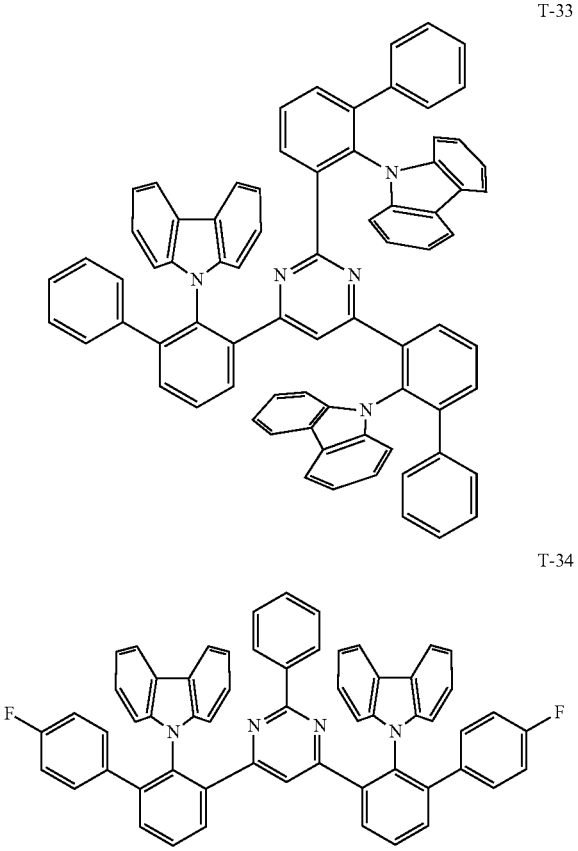
T-34
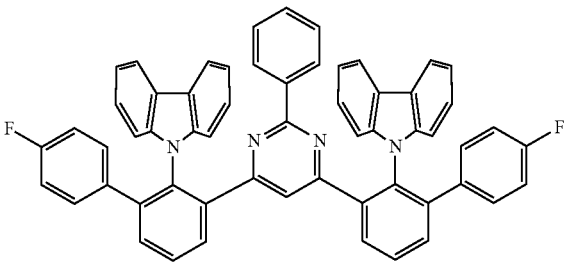
T-35
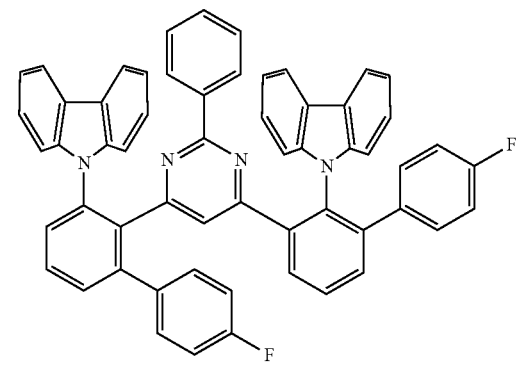
T-36
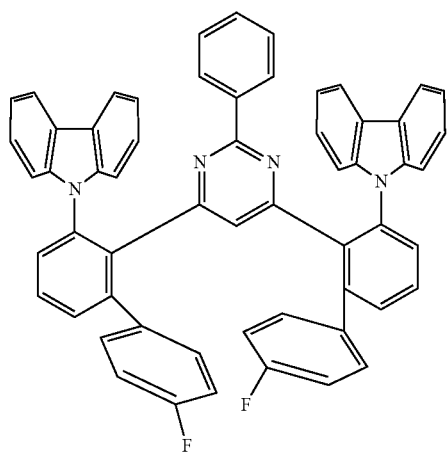
T-37
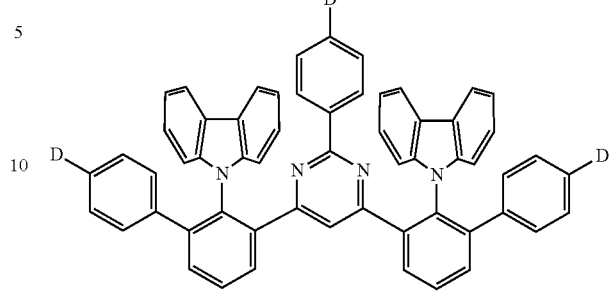
T-38
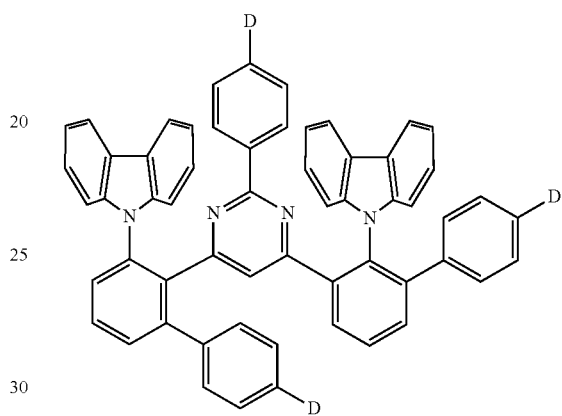
T-39
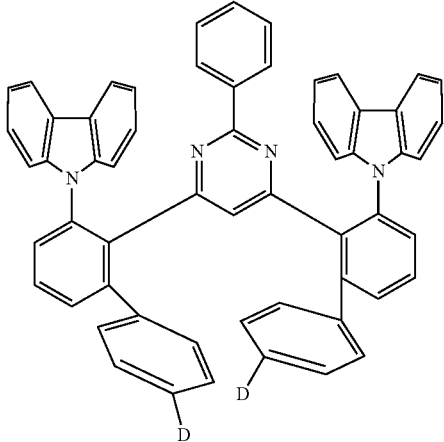
T-40
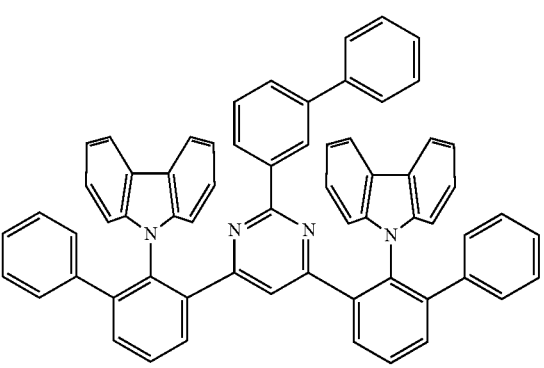

-continued
T-41
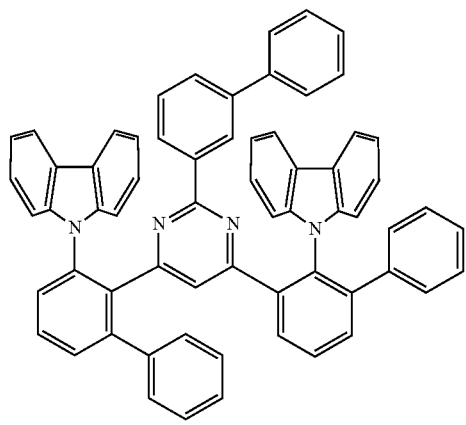
T-42
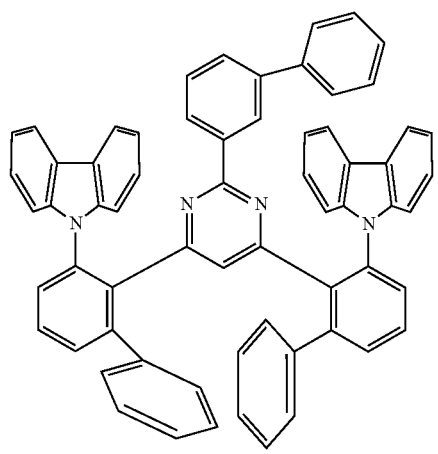
T-43
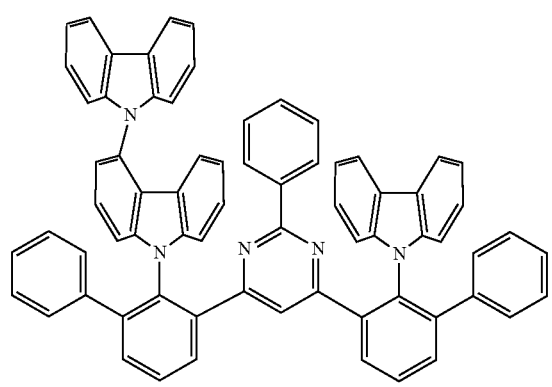
-continued
T-44
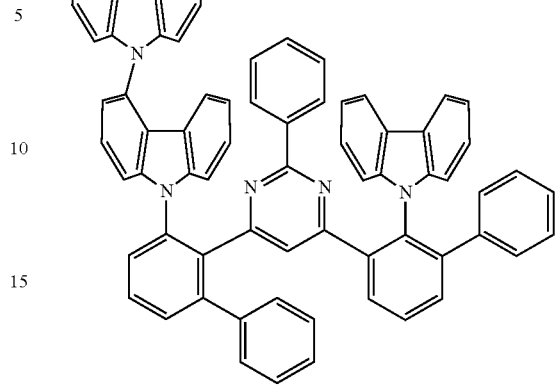
T-45
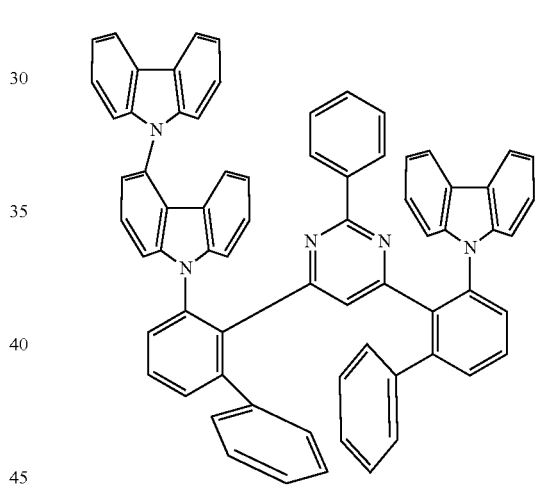
T-46
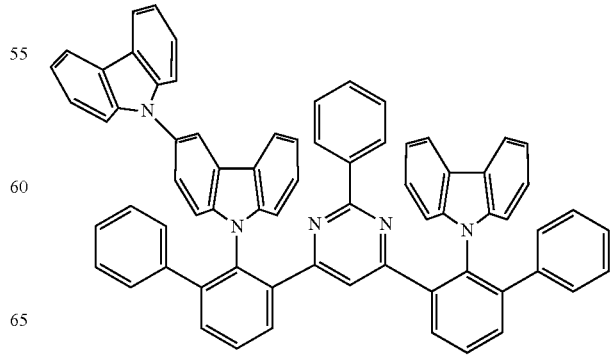

T-47
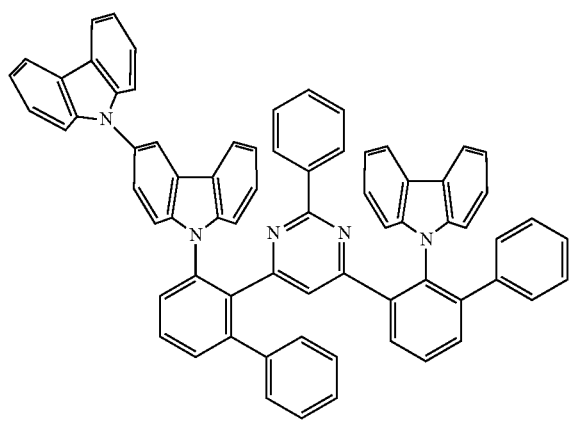
T-48
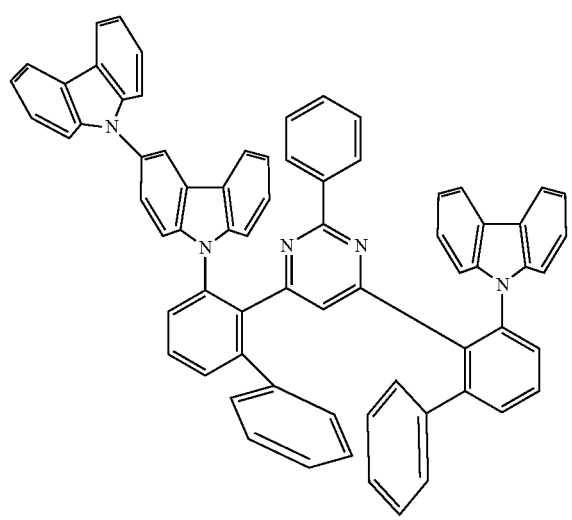
T-49
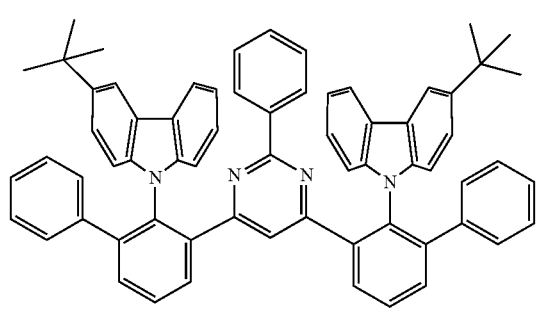
T-50
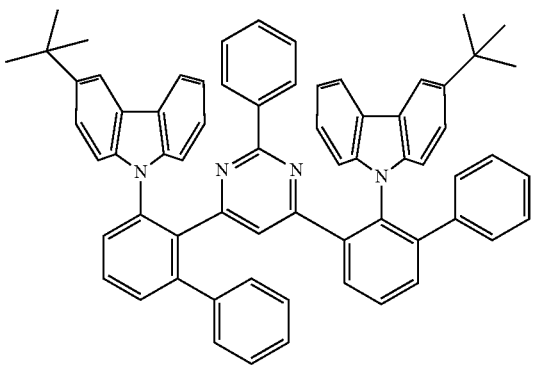
T-51
T-52
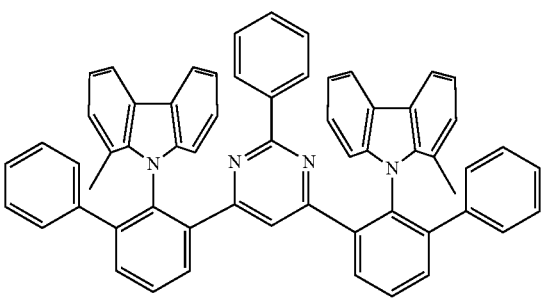
T-53

T-54

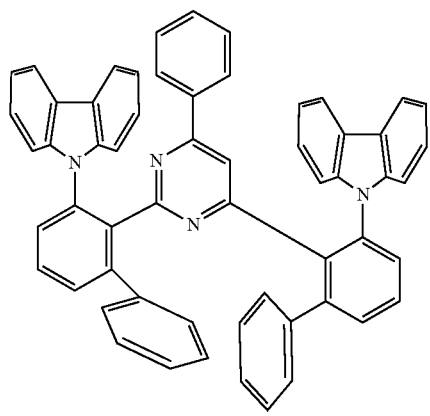

T-55

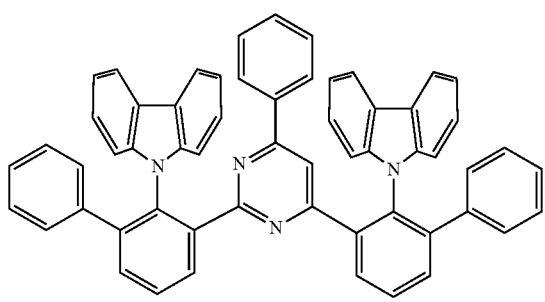

T-56

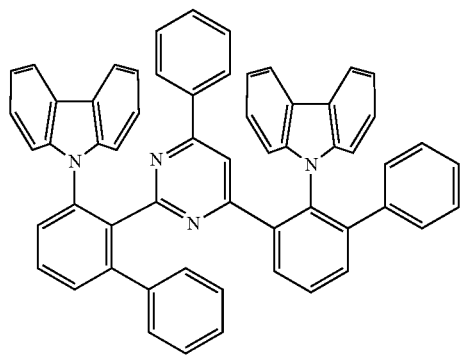

When the compound including nitrogen according to an embodiment of the present disclosure has a structure in which a phenylene group is substituted with a carbazole group and a phenyl group (e.g., a structure in which the N-phenyl of an N-phenyl carbazole is substituted with a phenyl group), an electron donor group and an electron acceptor group may be orthogonal (e.g., oriented so that the groups are structurally orthogonal), and the difference between a singlet energy level of the compound and a triplet energy level of the compound may approach 0 eV. Accordingly, the compound may be utilized as a material for thermally activated delayed fluorescence. In some embodiments, the compound including nitrogen according to an embodiment of the present disclosure may be applied as a light-emitting material that is to emit blue light having a wavelength region of less than about 470 nm, for example, as a light-emitting material that is to emit deep blue light having a wavelength region of about 440 nm to about 470 nm, or about 450 nm to about 470 nm.

Hereinafter, an organic electroluminescence device according to an embodiment of the present disclosure will be described in further detail. The description will focus mainly on features of the device that were not previously described in connection with the compound including nitrogen according to an embodiment of the present disclosure, and it will be understood that aspects and features of the compound including nitrogen according to an embodiment of the present disclosure may also be available in the organic electroluminescence device according to embodiments of the present disclosure.

The organic electroluminescence device according to an embodiment of the present disclosure includes the above-described compound including nitrogen according to an embodiment of the present disclosure.

Figure 2:
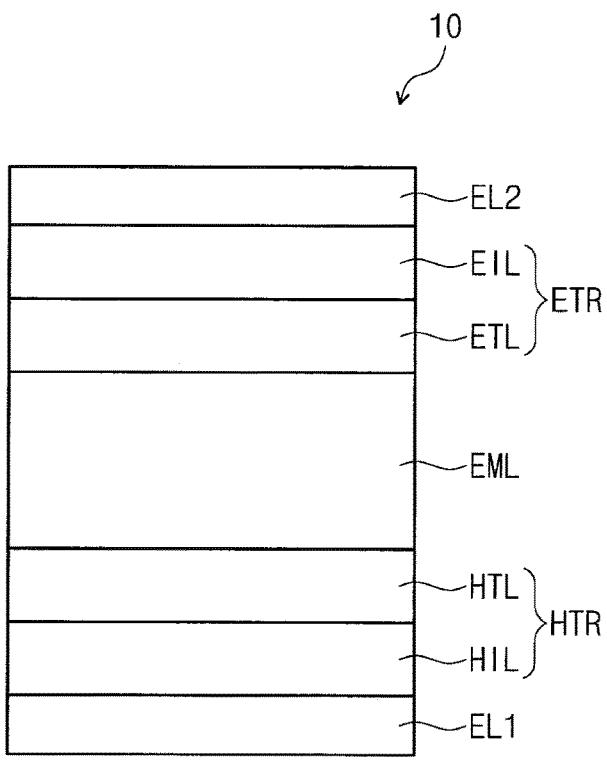
FIG. 2 is a cross-sectional view schematically illustrating an organic electroluminescence device according to an embodiment of the present disclosure.
Figure 3:
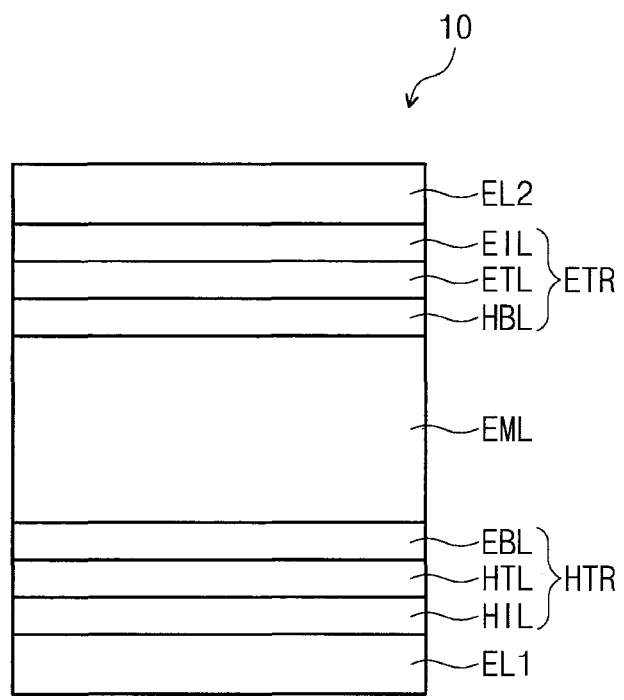
FIG. 3 is a cross-sectional view schematically illustrating an organic electroluminescence device according to an embodiment of the present disclosure.

FIG. 1 is a cross-sectional view schematically illustrating an organic electroluminescence device according to an embodiment of the present disclosure. FIG. 2 is a cross-sectional view schematically illustrating an organic electroluminescence device according to an embodiment of the present disclosure. FIG. 3 is a cross-sectional view schematically illustrating an organic electroluminescence device according to an embodiment of the present disclosure.

Referring to FIGS. 1 to 3, an organic electroluminescence device 10 according to an embodiment of the present disclosure may include a first electrode EL1, a hole transport region HTR, an emission layer EML, an electron transport region ETR, and a second electrode EL2.

The first electrode EL1 may have conductivity (e.g., may be conductive). The first electrode EL1 may be a pixel electrode or an anode. The first electrode EL1 may be a transmissive electrode, a transflective electrode, or a reflective electrode. When the first electrode EL1 is a transmissive electrode, the first electrode EL1 may include a transparent metal oxide, for example, indium tin oxide (ITO), indium zinc oxide (IZO), zinc oxide (ZnO), indium tin zinc oxide (ITZO), and/or the like. When the first electrode EL1 is a transflective electrode or a reflective electrode, the first electrode EL1 may include silver (Ag), magnesium (Mg), copper (Cu), aluminum (Al), platinum (Pt), palladium (Pd), gold (Au), nickel (Ni), neodymium (Nd), iridium (Ir), chromium (Cr), lithium (Li), calcium (Ca), lithium fluoride (LiF)/Ca, LiF/Al, molybdenum (Mo), titanium (Ti), a compound thereof, or a mixture thereof (for example, a mixture of Ag and Mg). Also, the first electrode EL1 may include a plurality of layers including a reflective layer and/or a transflective layer formed using the above materials, and/or a transparent layer formed using ITO, IZO, ZnO, and/or ITZO. For example, the first electrode EL1 may have a three-layer structure of ITO/Ag/ITO. However, embodiments of the present disclosure are not limited thereto.

The thickness of the first electrode EL1 may be about 1,000 Å to about 10,000 Å, for example, about 1,000 Å to about 3,000 Å.

The hole transport region HTR may be provided on the first electrode EL1. The hole transport region HTR may include at least one of a hole injection layer HIL, a hole transport layer HTL, a hole buffer layer, and/or an electron blocking layer.

The hole transport region HTR may have a single layer formed using a single material, a single layer formed using a plurality of different materials, or a multilayer structure including a plurality of layers formed using a plurality of different materials.

For example, the hole transport region HTR may have the structure of a single layer (such as a hole injection layer HIL or a hole transport layer HTL), or may have a structure of a single layer formed using a hole injection material and a hole transport material. In some embodiments, the hole transport region HTR may have a structure of a single layer formed using a plurality of different materials, or a structure including multiple layers laminated one by one on the first electrode EL1, for example, a structure of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer EBL, without limitation.

The hole transport region HTR may be formed using any suitable method (such as a vacuum deposition method, a spin coating method, a cast method, a Langmuir-Blodgett (LB) method, an inkjet printing method, a laser printing method, and/or a laser induced thermal imaging (LITI) method).

The hole injection layer HIL may include, for example, a phthalocyanine compound (such as copper phthalocyanine); N,N'-diphenyl-N,N'-bis-[4-(phenyl-m-tolyl-amino)-phenyl]-biphenyl-4,4'-diamine (DNTPD), 4,4',4''-tris(3-methylphenylphenylamino) triphenylamine (m-MTDATA), 4,4',4''-tris(N,N-diphenylamino)triphenylamine (TDATA), 4,4',4''-tris{N-(2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-dinaphthalene-1-yl)-N,N'-diphenyl-benzidine (NPD), triphenylamine-containing polyether ketone (TPAPEK), 4-isopropyl-4'-methyldiphenyliodonium tetrakis(pentafluorophenyl)borate, and/or dipyrazino[2,3-f: 2',3'-h] quinoxaline-2,3,6,7,10,11-hexacarbonitrile (HAT-CN), etc.

The hole transport layer HTL may include, for example, carbazole derivatives (such as N-phenyl carbazole and/or polyvinyl carbazole), fluorene-based derivatives, N,N'-bis (3-methylphenyl)-N,N'-diphenyl-[1,1-biphenyl]-4,4'-diamine (TPD), triphenylamine-based derivatives (such as 4,4',4''-tris(N-carbazolyl)triphenylamine (TCTA)), N,N'-di (1-naphthalene-1-yl)-N,N'-diphenyl-benzidine (NPD), 4,4'-cyclohexylidene bis[N,N-bis(4-methylphenyl)benzenamine] (TAPC), and/or 4,4'-bis[N,N'-(3-tolyl)amino]-3,3'-dimethylbiphenyl (HMTPD), etc.

The electron blocking layer EBL may include any suitable material available in the art. The electron blocking layer EBL may include, for example, carbazole derivatives (such as N-phenylcarbazole and/or polyvinyl carbazole), fluorene-based derivatives, N,N'-bis(3-methylphenyl)-N,N'-diphenyl-[1,1-biphenyl]-4,4'-diamine (TPD), triphenylamine-based derivatives (such as 4,4',4''-tris(N-carbazolyl) triphenylamine (TCTA)), N,N'-di(naphthalene-1-yl)-N,N'-diphenyl-benzidine (NPD), 4,4'-cyclohexylidene bis[N, N-bis(4-methylphenyl)benzenamine] (TAPC), 4,4'-bis[N, N'-(3-tolyl)amino]-3,3'-dimethylbiphenyl (HMTPD), and/or mCP, etc. In some embodiments, as described above, the electron blocking layer EBL may include the compound including nitrogen according to an embodiment of the present disclosure.

The thickness of the hole transport region HTR may be about 100 Å to about 10,000 Å, for example, about 100 Å to about 5,000 Å. The thickness of the hole injection layer HIL may be, for example, about 30 Å to about 1,000 Å, and the thickness of the hole transport layer HTL may be about 30 Å to about 1,000 Å. For example, the thickness of the electron blocking layer EBL may be about 10 Å to about 1,000 Å. When the thicknesses of the hole transport region HTR, the hole injection layer HIL, the hole transport layer HTL, and the electron blocking layer EBL satisfy the above-described ranges, satisfactory hole transport properties may be obtained without a substantial increase in driving voltage.

The hole transport region HTR may further include a charge generating material in addition to the above-described materials to improve conductivity. The charge generating material may be uniformly or non-uniformly dispersed in the hole transport region HTR. The charge generating material may be, for example, a p-dopant. The p-dopant may be a quinone derivative, metal oxide, or cyano group-containing compound, although embodiments of the present disclosure are not limited thereto. Non-limiting examples of the p-dopant may include quinone derivatives (such as tetracyanoquinodimethane (TCNQ) and/or 2,3,5,6-tetrafluoro-tetracyanoquinodimethane (F4-TCNQ)), and metal oxides (such as tungsten oxide and/or molybdenum oxide).

As described above, the hole transport region HTR may further include at least one of a hole buffer layer and/or an electron blocking layer EBL. The hole buffer layer may compensate for a resonance distance according to the wavelength of light emitted from the emission layer EML, and thereby increase light emission efficiency. The materials included in the hole transport region HTR may also be used as materials in the hole buffer layer. The electron blocking layer EBL may prevent or reduce electron injection from the electron transport region ETR to the hole transport region HTR.

The emission layer EML may be provided on the hole transport region HTR. The thickness of the emission layer EML may be, for example, about 100 Å to about 1,000 Å, or about 100 Å to about 300 Å. The emission layer EML may have the structure of a single layer formed using a single material, the structure of a single layer formed using a plurality of different materials, or a multilayer structure including a plurality of layers formed using a plurality of different materials.

Hereinafter, an embodiment including the compound including nitrogen according to an embodiment of the present disclosure in an emission layer EML will be explained. However, embodiments of the present disclosure are not limited thereto.

The compound including nitrogen according to an embodiment of the present disclosure may be included in at least one layer among the one or more organic layers provided between a first electrode EL1 and a second electrode EL2. In some embodiments, for example, the compound including nitrogen according to an embodiment of the present disclosure may be included in a hole transport region HTR. In some embodiments, the compound including nitrogen according to an embodiment of the present disclosure may be included in a hole transport layer HTL or an electron blocking layer EBL.

An emission layer EML may include the compound including nitrogen according to an embodiment of the present disclosure. For example, the emission layer EML may include a compound including nitrogen, represented by Formula 1:

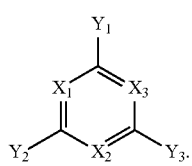

Formula 1

In Formula 1, $X_1$ to $X_3$ and $Y_1$ to $Y_3$ may be the same as described above.

The emission layer EML may include one, or two or more types or kinds of the compound including nitrogen represented by Formula 1. The emission layer EML may further include any suitable material (e.g. a material available in the related art), in addition to the compound including nitrogen represented by Formula 1. For example, a fluorescent material selected from the group consisting of spiro-DPVBi, 2,2',7,7'-tetrakis(biphenyl-4-yl)-9,9'-spirobifluorene (spiro-6P, spiro-sexiphenyl), distyryl-benzene (DSB), distyrylarylene (DSA), a polyfluorene (PFO)-based polymer, and a poly(p-phenylene vinylene) (PPV)-based polymer. However, embodiments of the present disclosure are not limited thereto.

The emission layer EML may include a host and a dopant, and the dopant may include the compound including nitrogen according to an embodiment of the present disclosure. The emission layer EML may include one type or kind of dopant. However, embodiments of the present disclosure are not limited thereto. In some embodiments, the dopant may include a first dopant and a second dopant. The first dopant or the second dopant may include the compound including nitrogen according to an embodiment of the present disclosure. For example, the first dopant may include the compound including nitrogen according to an embodiment of the present disclosure, and the second dopant may include any suitable dopant material. The doping concentration of the first dopant may be greater than the doping concentration of the second dopant in the emission layer EML. The second dopant may be, for example, TBP, but embodiments of the present disclosure are not limited thereto.

The emission layer EML may be an emission layer that is to emit thermally activated delayed fluorescence. For example, the emission layer EML may be a blue emission layer that is to emit blue light via thermally activated delayed fluorescence.

The host may be any suitable material available in the related art, for example, tris(8-hydroxyquinolino)aluminum ($Alq_3$), 4,4'-bis(N-carbazolyl)-1,1'-biphenyl (CBP), poly(n-vinylcarbazole) (PVK), 9,10-di(naphthalene-2-yl)anthracene (ADN), 4,4',4''-tris(carbazol-9-yl)-triphenylamine (TCTA), 1,3,5-tris(N-phenylbenzimidazole-2-yl)benzene (TPBi), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), bis[2-(diphenylphosphino)phenyl] ether oxide (DPEPO), hexaphenyl cyclotriphosphazene (CP1), 1,4-bis(triphenylsilyl)benzene (UGH2), hexaphenylcyclotrisiloxane ($DPSiO_3$), octaphenylcyclotetra siloxane ($DPSiO_4$), and/or 2,8-bis(diphenylphosphoryl)dibenzofuran (PPF), etc., but embodiments of the present disclosure are not limited thereto.

The electron transport region ETR may be provided on the emission layer EML. The electron transport region ETR may include at least one of a hole blocking layer HBL, an electron transport layer ETL, and/or an electron injection layer EIL, without limitation.

The electron transport region ETR may have the structure of a single layer formed using a single material, a single layer formed using a plurality of different materials, or a multilayer structure including a plurality of layers formed using a plurality of different materials.

For example, the electron transport region ETR may have the structure of a single layer (such as an electron injection layer EIL or an electron transport layer ETL), or a single layer structure formed using an electron injection material and an electron transport material. In some embodiments, the electron transport region ETR may have a single layer structure formed using a plurality of different materials, or a structure including multiple layers laminated one by one on the emission layer EML, for example, a structure of electron transport layer ETL/electron injection layer EIL, or hole blocking layer HBL/electron transport layer ETL/electron injection layer EIL, without limitation. The thickness of the electron transport region ETR may be, for example, about 1,000 Å to about 1,500 Å.

The electron transport region ETR may be formed using any suitable method (such as a vacuum deposition method, a spin coating method, a cast method, a Langmuir-Blodgett (LB) method, an inkjet printing method, a laser printing method, and/or a laser induced thermal imaging (LITI) method).

When the electron transport region ETR includes an electron transport layer ETL, the electron transport region ETR may include tris(8-hydroxyquinolinato)aluminum ($Alq_3$), 1,3,5-tri[(3-pyridyl)-phen-3-yl]benzene, 2,4,6-tris(3'-(pyridin-3-yl)biphenyl-3-yl)-1,3,5-triazine, bis[2-(diphenylphosphino)phenyl]ether oxide (DPEPO), 2-(4-(N-phenylbenzoimidazolyl-1-ylphenyl)-9,10-dinaphthylanthracene, 1,3,5-tri(1-phenyl-1H-benzo[d]imidazol-2-yl)phenyl (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato) aluminum (BAlq), berylliumbis(benzoquinolin-10-olate ($Bebq_2$), 9,10-di(naphthalene-2-yl)anthracene (ADN), or a mixture thereof, without limitation. The thickness of the electron transport layer ETL may be about 100 Å to about 1,000 Å, for example, about 150 Å to about 500 Å. When the thickness of the electron transport layer ETL satisfies the above-described range, satisfactory electron transport properties may be obtained without a substantial increase in driving voltage.

When the electron transport region ETR includes an electron injection layer EIL, the electron transport region ETR may include LiF, lithium quinolate (LiQ), $Li_2O$, BaO, NaCl, CsF, a lanthanide metal (such as ytterbium (Yb)), or a metal halide (such as RbCl and/or RbI), without limitation. The electron injection layer EIL also may be formed using a mixture of an electron transport material and an insulating organometallic salt. The organometallic salt may be a material having an energy band gap of about 4 eV or more. The organometallic salt may include, for example, a metal acetate, a metal benzoate, a metal acetoacetate, a metal acetylacetonate, and/or a metal stearate. The thickness of the electron injection layer EIL may be about 1 Å to about 100 Å, or about 3 Å to about 90 Å. When the thickness of the electron injection layer EIL satisfies the above described range, satisfactory electron injection properties may be obtained without inducing a substantial increase in driving voltage.

The electron transport region ETR may include a hole blocking layer HBL, as described above. The hole blocking layer HBL may include, for example, 2,9-dimethyl-4,7-diphenyl-1,10-phenanthroline (BCP), 4,7-diphenyl-1,10-phenanthroline (Bphen), and/or bis[2-(diphenylphosphino)phenyl]ether oxide (DPEPO), etc. without limitation.

The second electrode EL2 may be provided on the electron transport region ETR. The second electrode EL2 may be a common (e.g., shared) electrode or a cathode. The second electrode EL2 may be a transmissive electrode, a transflective electrode, or a reflective electrode. When the second electrode EL2 is a transmissive electrode, the second electrode EL2 may include a transparent metal oxide, for example, ITO, IZO, ZnO, ITZO, etc.

When the second electrode EL2 is a transflective electrode or a reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). The second electrode EL2 may include a plurality of layers including a reflective layer and/or a transflective layer formed using the above materials, and/or a transparent conductive layer formed using ITO, IZO, ZnO, or ITZO.

In some embodiments, the second electrode EL2 may be connected to an auxiliary electrode. When the second electrode EL2 is connected to an auxiliary electrode, the resistance of the second electrode EL2 may be decreased.

In the organic electroluminescence device 10, voltages may be applied to each of the first electrode EL1 and the second electrode EL2, and holes injected into the device move from the first electrode EL1 via the hole transport region HTR to the emission layer EML, while electrons injected into the device move from the second electrode EL2 via the electron transport region ETR to the emission layer EML. The electrons and holes recombine in the emission layer EML to generate excitons, and the excitons may emit light upon transitioning from an excited state to the ground state.

When the organic electroluminescence device 10 is a top emission type (e.g., top emission device), the first electrode EL1 may be a reflective electrode, and the second electrode EL2 may be a transmissive electrode or a transflective electrode. When the organic electroluminescence device 10 is a bottom emission type (e.g., bottom emission device), the first electrode EL1 may be a transmissive electrode or a transflective electrode, and the second electrode EL2 may be a reflective electrode.

The organic electroluminescence device 10 according to an embodiment of the present disclosure may include the compound including nitrogen, represented by Formula 1, and may thereby exhibit an increased lifespan and efficiency while being to emit blue light (for example, deep blue light emission) at the same time.

Hereinafter, the present disclosure will be explained in more detail by referring to example embodiments and comparative embodiments. The following embodiments are included only for illustration and to assist in understanding of the present disclosure, and the scope of the present disclosure is not limited thereto.

SYNTHETIC EXAMPLES

The compound including nitrogen according to an embodiment of the present disclosure may be synthesized according to the following example. However, methods of synthesizing the compound including nitrogen according to an embodiment of the present disclosure are not limited thereto.

1. Synthesis of Compound T-01

Compound T-01 which is a compound including nitrogen according to an embodiment of the present disclosure may be synthesized by the following example reaction:

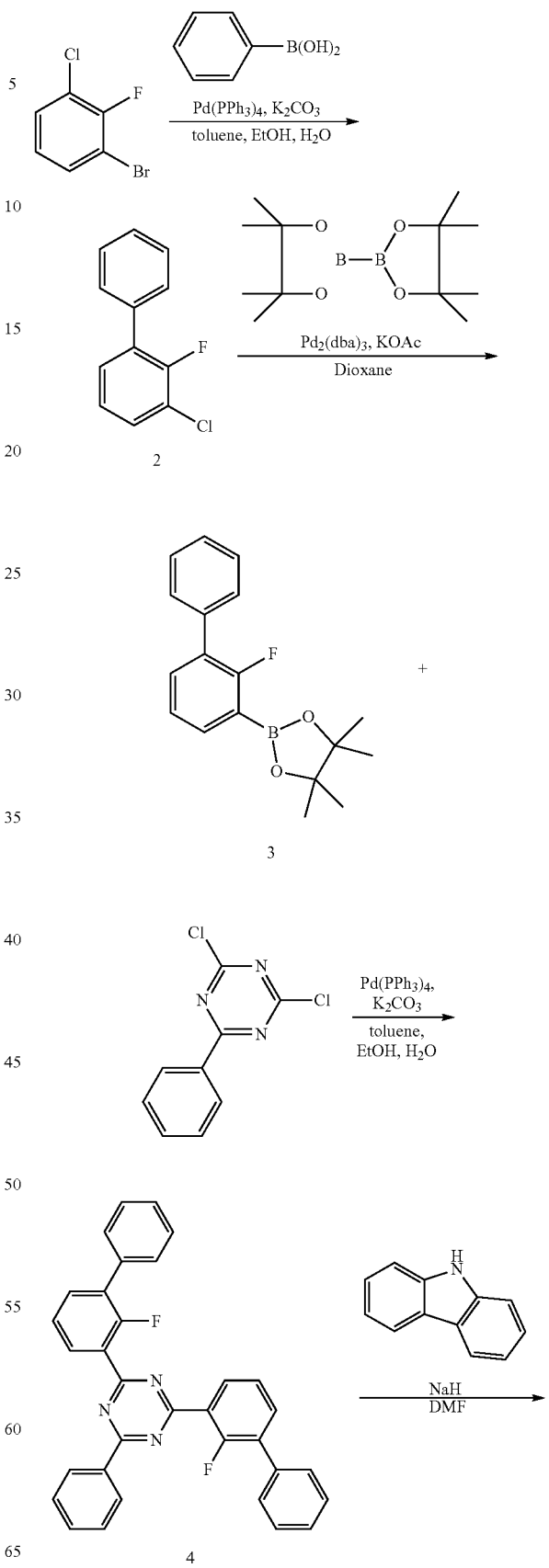

T-01

Synthesis of Compound 2

Under an argon (Ar) atmosphere, in a 500 mL three-neck flask, 35.0 g of 1-bromo-3-chloro-2-fluorobenzene, 26.5 g of phenylboronic acid, 46.2 g of $K_2CO_3$, and 1,000 mL of a mixed solution of toluene/EtOH/water (7:1:2) in which 5.79 g of Pd(PPh$_3$)$_4$ was dissolved, were heated and stirred at about 80° C. for about 5 hours. After cooling in the air, dichloromethane was added, the organic layers were collected, and the solvents were removed. The crude product thus obtained was separated by silica gel chromatography (using hexane) to obtain 30.0 g (yield 87%) of Compound 2 as a transparent oil.

The molecular weight of Compound 2 measured by GC-MS was 206.

Synthesis of Compound 3

Under an argon (Ar) atmosphere, in a 2 L three-neck flask, 30.0 g of Compound 2, 47.9 g of bis(pinacolato)diboron, 31.3 g of KOAc, and 1,000 mL of a dioxane solution in which 5.31 g of Pd$_2$(dba)$_3$ was dissolved, were heated and stirred at about 100° C. for about 5 hours. After cooling in the air, dichloromethane was added, the organic layers were collected, and the solvents were removed. The crude product thus obtained was separated by silica gel chromatography (using toluene) to obtain 38.6 g (yield 89%) of Compound 3 as a transparent oil.

The molecular weight of Compound 3 measured by FAB-MS was 298.

Synthesis of Compound 4

Under an argon (Ar) atmosphere, in a 2 L three-neck flask, 14.0 g of 2,4-dichloro-6-phenyl-1,3,5-triazine, 38.8 g of Compound 3, 34.3 g of $K_2CO_3$, and 1,000 mL of a mixed solution of toluene/EtOH/water (7:1:2) in which 4.29 g of Pd(PPh$_3$)$_4$ was dissolved, were heated and stirred at about 80° C. for about 5 hours. After cooling in the air, the crude product was separated to obtain 24.0 g (yield 78%) of Compound 4 as a white solid.

The molecular weight of Compound 4 measured by FAB-MS was 497.

Synthesis of Compound T-01

Under an argon (Ar) atmosphere, in a 200 mL three-neck flask, 17.7 g of carbazole, 24.0 g of Compound 4, and 800 mL of a DMF solution in which 4.79 g of NaH was dissolved, were heated and stirred at about 120° C. for about 5 hours. After cooling in the air, the precipitate was filtered, washed with water, EtOH and toluene, and recrystallized from toluene/EtOH to produce 23.1 g (yield 84ˆ) of Compound T-01 as a pale yellow solid.

The molecular weight of T-01 measured by FAB-MS was 792.

$^1$H NMR (CDCl$_3$, 25° C., 300 Hz) δ=6.812 (d, 2H, J=8 Hz), 6.899 (t, 2H, J=15 Hz), 6.975 (d, 4H, J=8 Hz), 7.139-7.273 (m, 9H), 7.363 (t, 4H, J=15 Hz), 7.498 (t, 2H, J=15 Hz), 7.577 (d, 2H, J=8 Hz), 7.651-7.755 (m, 8H), 7.989 (d, 4H, J=8 Hz).

2. Synthesis of Compound T-04

Compound T-04 was synthesized using substantially the same method used for Compound T-01, except for using 1-bromo-2-chloro-3-fluorobenzene instead of (e.g., in place of) 1-bromo-3-chloro-2-fluorobenzene.

The molecular weight of T-04 measured by FAB-MS was 792.

$^1$H NMR (CDCl$_3$, 25° C. 300 Hz) δ=6.828 (d, 2H, J=8 Hz), 6.899 (t, 2H, J=15 Hz), 6.926 (d, 4H, J=8 Hz), 7.139-7.273 (m, 9H), 7.343 (t, 4H, J=14 Hz), 7.498 (t, 2H, J=15 Hz), 7.597 (d, 2H, J=8 Hz), 7.682-7.721 (m, 8H), 7.889 (d, 4H, J=8 Hz)

3. Synthesis of Compound T-05

Compound T-05 was synthesized using substantially the same method used for Compound T-01, except for using cyanuric chloride instead of 2,4-dichloro-6-phenyl-1,3,5-triazine.

The molecular weight of T-05 measured by FAB-MS was 1,033.

$^1$H NMR (CDCl$_3$, 25° C. 300 Hz) δ=6.828 (d, 2H, J=7 Hz), 6.901 (t, 2H, J=15 Hz), 6.934 (d, 4H, J=7 Hz), 7.149-7.288 (m, 15H), 7.363 (t, 4H, J=14 Hz), 7.528 (t, 2H, J=15 Hz), 7.617 (d, 2H, J=8 Hz), 7.666-7.732 (m, 13H), 7.999 (d, 4H, J=8 Hz).

4. Synthesis of Compound T-06

Compound T-06 was synthesized using substantially the same method as for Compound T-01, except for using 4-fluorophenylboronic acid instead of phenylboronic acid.

The molecular weight of T-06 measured by FAB-MS was 828.

$^1$H NMR (CDCl$_3$, 25° C., 300 Hz) δ=6.722 (d, 2H, J=8 Hz), 6.889 (t, 2H, J=15 Hz), 6.945 (d, 4H, J=8 Hz), 7.139-7.273 (m, 7H), 7.367 (t, 4H, J=15 Hz), 7.448 (t, 2H, J=14 Hz), 7.577 (d, 2H, J=7 Hz), 7.650-7.755 (m, 8H), 7.909 (d, 4H, J=7 Hz).

5. Synthesis of Compound T-21

Compound T-21 was synthesized using substantially the same method as for Compound T-01, except for using 3-tert-butylcarbazole instead of carbazole.

The molecular weight of T-21 measured by FAB-MS was 904.

$^1$H NMR (CDCl$_3$, 25° C., 300 Hz) δ=1.479 (s, 18H) 6.828 (d, 2H, J=7 Hz), 6.934 (d, 4H, J=7 Hz), 7.149-7.288 (m, 15H), 7.363 (t, 4H, J=14 Hz), 7.528 (t, 2H, J=15 Hz), 7.617 (d, 2H, J=8 Hz), 7.666-7.732 (m, 13H), 7.999 (d, 4H, J=8 Hz).

6. Synthesis of Compound T-29

Compound T-29 was synthesized using substantially the same method as for Compound T-01, except for using fenclorim instead of 2,4-dichloro-6-phenyl-1,3,5-triazine.

The molecular weight of T-29 measured by FAB-MS was 791.

$^1$H NMR (CDCl$_3$, 25° C., 300 Hz) δ=6.822 (d, 2H, J=8 Hz), 6.901 (t, 2H, J=15 Hz), 6.973 (d, 4H, J=8 Hz), 7.133-7.284 (m, 10H), 7.377 (t, 4H, J=15 Hz), 7.508 (t, 2H, J=15 Hz), 7.582 (d, 2H, J=8 Hz), 7.666-7.762 (m, 8H), 7.990 (d, 4H, J=8 Hz).

Device Manufacturing Example 1

The organic electroluminescence devices of Examples 1 to 6 were manufactured using Compounds T-01, T-04, T-05, T-06, T-21, and T-29 as dopant materials in each emission layer.

Example Compounds

T-01

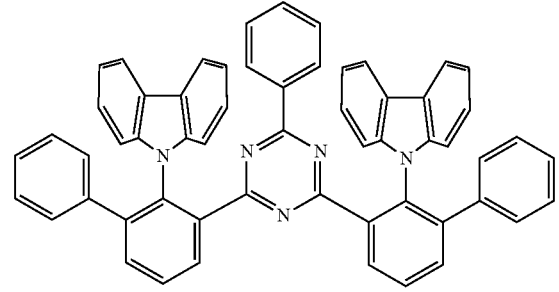

T-04

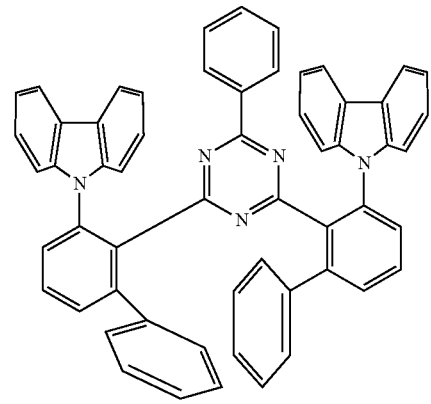

T-05

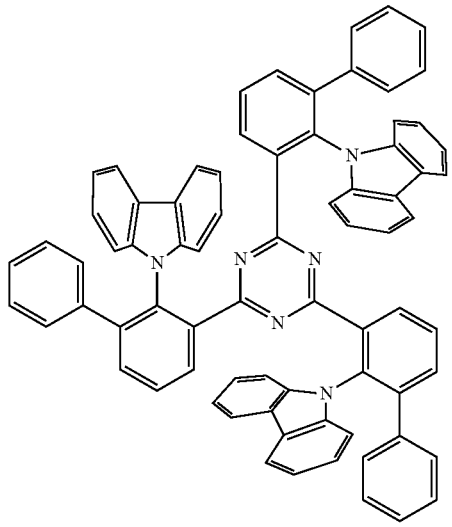

T-06

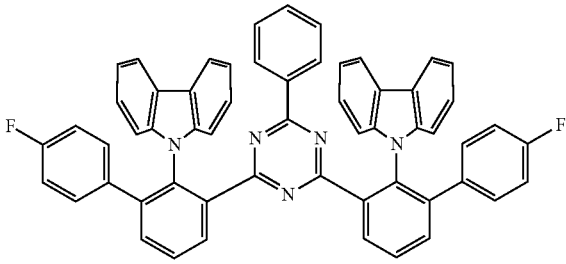

T-21

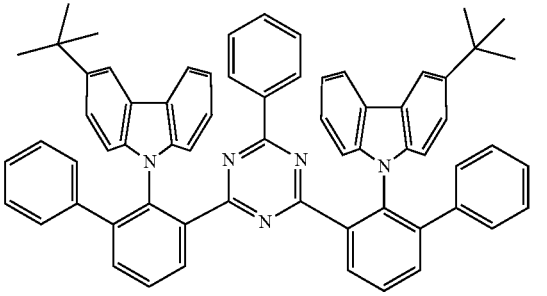

T-29

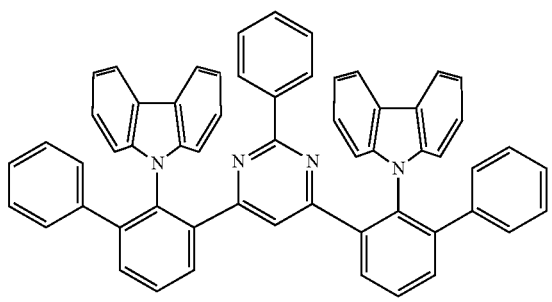

The organic electroluminescence devices of Comparative Examples 1 to 4 were manufactured using Comparative Compounds E-1 to E-4 as dopant materials in each emission layer.

Comparative Compounds

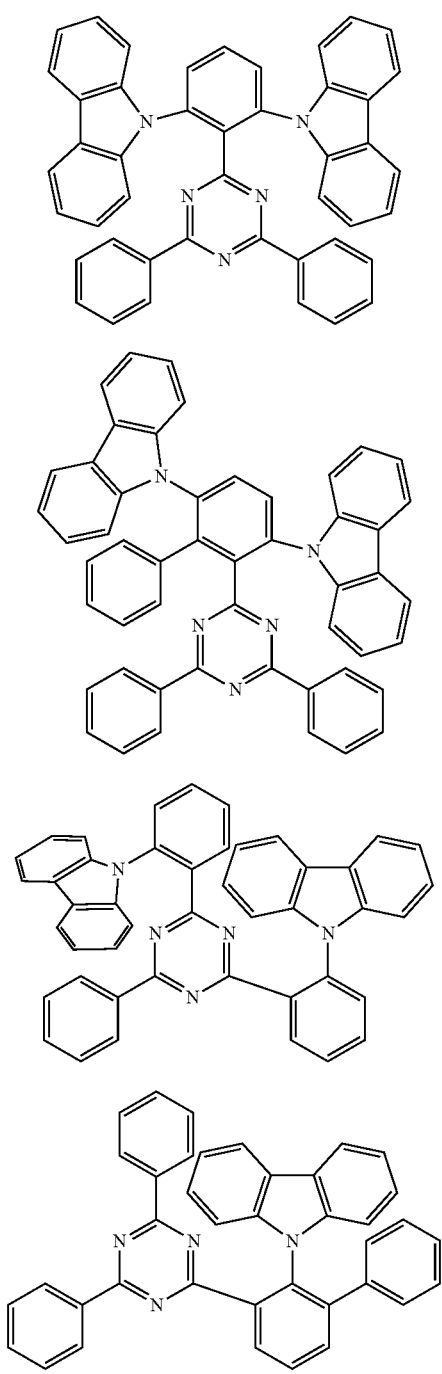

The organic electroluminescence devices of Examples 1 to 6 and Comparative Examples 1 to 4 were manufactured as follows. A first electrode with a thickness of about 150 nm was formed using ITO, a hole injection layer with a thickness of about 10 nm was formed using HAT-CN, a hole transport layer with a thickness of about 80 nm was formed using α-NPD, an electron blocking layer with a thickness of about 5 nm was formed using mCP, an emission layer with a thickness of about 20 nm was formed using DPEPO doped with 20% of one of the example compounds or the comparative compounds, a hole blocking layer with a thickness of about 10 nm was formed using DPEPO, an electron transport layer with a thickness of about 30 nm was formed using TPBi, an electron injection layer with a thickness of about 0.5 nm was formed using LiF, and a second electrode with a thickness of about 100 nm was formed using Al. Each layer was formed using a vacuum deposition method.

TABLE 1

|  | Dopant of emission layer | λmax (nm) | EQE (%) | Life LT50 (h) |
|---|---|---|---|---|
| Example 1 | Example Compound T-01 | 465 | 18.5 | 19.5 |
| Example 2 | Example Compound T-04 | 462 | 18.0 | 21.0 |
| Example 3 | Example Compound T-05 | 463 | 17.9 | 19.5 |
| Example 4 | Example Compound T-06 | 465 | 18.0 | 20.0 |
| Example 5 | Example Compound T-21 | 466 | 18.2 | 20.0 |
| Example 6 | Example Compound T-29 | 462 | 18.2 | 20.05 |
| Comparative Example 1 | Comparative Compound E-1 | 455 | 12.5 | 10.0 |
| Comparative Example 2 | Comparative Compound E-2 | 470 | 11.5 | 12.0 |
| Comparative Example 3 | Comparative Compound E-3 | 475 | 10.5 | 15.5 |
| Comparative Example 4 | Comparative Compound E-4 | 475 | 10.0 | 13.5 |

In the above table, "Life LT50" refers to a time required for the luminance of the device to fall to half of its initial luminance of 100 cd/cm², and "EQE" refers to the external quantum efficiency value at 10 mA/cm².

Referring to Table 1, it may be found that the organic electroluminescence devices according to Examples 1 to 6 emitted deep blue light and had increased efficiency and lifespans, compared to the organic electroluminescence devices according to Comparative Examples 1 to 4. In the example compounds, since the carbazole substituted phenylene group is additionally substituted with a phenyl group, and an electron donor and an electron acceptor are orthogonal (e.g., structurally orthogonal), the difference between a singlet energy level of the compound and a triplet energy level of the compound approached 0 eV, and thus, efficiency was improved and the emission wavelength was decreased. In addition, the example compounds have a longer pi conjugation system due to the phenyl group substituted at the phenylene group, thus further stabilizing the excited state.

In Comparative Examples 1 and 2, the comparative compounds are sterically overcrowded and are liable to decompose (e.g., are sterically unstable and thereby prone to degradative side reactions), and the devices including these compounds thus have short lifetimes. In Comparative Example 3, the twisted degree of a carbazole group is small (e.g., the dihedral angle between the phenylene group and the carbazolyl substituent is comparatively small in the absence of the phenyl substituent ortho to the carbazolyl group), such that the difference between a singlet energy level of the compound and a triplet energy level of the compound becomes large and the efficiency is low. Accordingly, charge balance is collapsed and the lifespan is decreased. In Comparative Example 4, since an electron donor is one (e.g., the compound includes one carbazole substituent instead of two), the substituting effect of a phenyl group at the carbazole substituted phenylene group is small.

The singlet energy level, the triplet energy level, and the difference (EST) between the singlet and triplet energy levels of each of the example compounds and the comparative compounds used in Examples 1 to 6 and Comparative Examples 1 to 4 are listed in Table 2.

TABLE 2

| | Dopant of emission layer | $S_1$ (eV) | $T_1$ (eV) | $E_{ST}$ (eV) |
|---|---|---|---|---|
| Example 1 | Example Compound T-01 | 2.90 | 2.85 | 0.05 |
| Example 2 | Example Compound T-04 | 3.11 | 3.03 | 0.08 |
| Example 3 | Example Compound T-05 | 2.75 | 2.70 | 0.05 |
| Example 4 | Example Compound T-06 | 2.72 | 2.68 | 0.04 |
| Example 5 | Example Compound T-21 | 2.67 | 2.63 | 0.04 |
| Example 6 | Example Compound T-29 | 2.90 | 2.86 | 0.04 |
| Comparative Example 1 | Comparative Compound E-1 | 3.07 | 2.99 | 0.08 |
| Comparative Example 2 | Comparative Compound E-2 | 3.01 | 2.96 | 0.05 |
| Comparative Example 3 | Comparative Compound E-3 | 2.84 | 2.78 | 0.06 |
| Comparative Example 4 | Comparative Compound E-4 | 2.92 | 2.87 | 0.05 |

The S1 level and T1 level of the example compounds and the comparative compounds were calculated by a non-empirical molecular orbital method and EST was obtained. For example, the results herein were calculated using the B3LYP functional and 6-31G(d) basis set using Gaussian09 (Gaussian Co., Wallingford, Conn.).

Device Manufacturing Example 2

The organic electroluminescence devices of Examples 7 to 12 were manufactured using Compounds T-01, T-04, T-05, T-06, T-21 and T-29 as first dopant materials of an emission layer.

The organic electroluminescence devices of Comparative Examples 5 to 8 were manufactured using Comparative Compounds E-5, E-6, E-3 and E-4 as first dopant materials of an emission layer.

Comparative Compounds

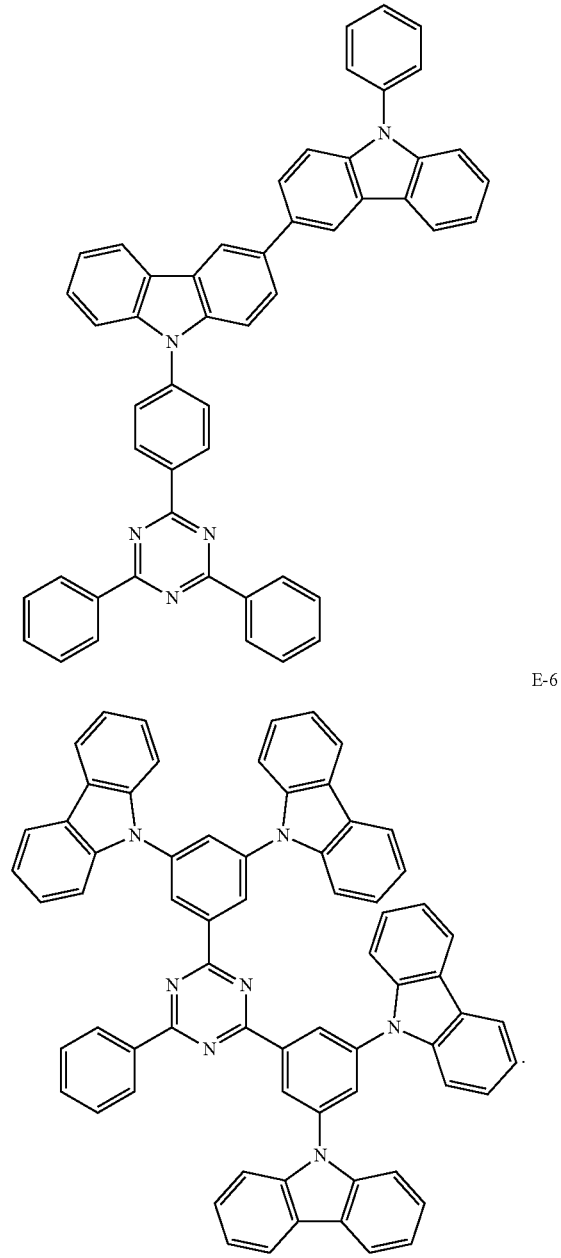

The organic electroluminescence devices of Examples 7 to 12 and Comparative Examples 5 to 8 were manufactured as follows. A first electrode with a thickness of about 150 nm was formed using ITO, a hole injection layer with a thickness of about 10 nm was formed using HAT-CN, a hole transport layer with a thickness of about 80 nm was formed using α-NPD, an electron blocking layer with a thickness of about 5 nm was formed using mCP, an emission layer with a thickness of about 20 nm was formed using DPEPO doped with 24% of one of the example compounds or the comparative compounds as a first dopant and doped with 1% of TBP as a second dopant, a hole blocking layer with a thickness of about 5 nm was formed using DPEPO, an electron transport layer with a thickness of about 20 nm was formed using TPBi, an electron injection layer with a thickness of about 0.5 nm was formed using LiF, and a second electrode with a thickness of about 80 nm was formed using Al. Each layer was formed by a vacuum deposition method.

In Table 3, "EQE" is the value at 10 mA/cm$^2$.

TABLE 3

|  | First dopant of emission layer | λmax (nm) | EQE (%) |
|---|---|---|---|
| Example 7 | Example Compound T-01 | 462 | 18.5 |
| Example 8 | Example Compound T-04 | 461 | 18.0 |
| Example 9 | Example Compound T-05 | 463 | 18.0 |
| Example 10 | Example Compound T-06 | 462 | 17.0 |
| Example 11 | Example Compound T-21 | 461 | 17.5 |
| Example 12 | Example Compound T-29 | 462 | 17.5 |
| Comparative Example 5 | Comparative Compound E-5 | 462 | 10.5 |
| Comparative Example 6 | Comparative Compound E-6 | 470 | 8.5 |
| Comparative Example 7 | Comparative Compound E-3 | 475 | 8.5 |
| Comparative Example 8 | Comparative Compound E-4 | 475 | 12.5 |

In Examples 7 to 12, the example compounds were used as the first dopant, and light emission was achieved by the second dopant, TBP (e.g., light is emitted by the TBP molecule).

Referring to Table 3, it may be found that the organic electroluminescence devices according to Examples 7 to 12 had increased efficiency compared to the organic electroluminescence devices according to Comparative Examples 5 to 8.

Since the carbazole substituted phenylene group is substituted with a phenyl group and an electron donor and an electron acceptor are orthogonal, the difference between a singlet energy level of the compound and a triplet energy level of the compound approaches 0. Accordingly, contributes to the light emission efficiency of the fluorescent dopant may be increased.

In Comparative Examples 5 to 7, the twist of a carbazole group is small (e.g., the dihedral angle between the phenylene group and the carbazolyl group substituent is relatively small), such that the difference between a singlet energy level of the compound and a triplet energy level of the compound is large, and the resulting efficiency is low. In Comparative Example 8, an electron donor is one (e.g., the compound includes one carbazole substituent instead of two), and substituting effect of a phenyl group with respect to a carbazole group substituted phenyl group is small.

Organic luminescence devices including the compound including nitrogen according to an embodiment of the present disclosure may have improved lifespan and efficiency compared to devices in the related art. The compound including nitrogen according to an embodiment of the present disclosure may also enable deep blue emission in addition to the improved lifespan and efficiency.

The compound including nitrogen according to an embodiment of the present disclosure may be used as a material of an organic layer in an organic electroluminescence device, and by using the compound, the efficiency of the organic electroluminescence device may be improved.

As used herein, expressions such as "at least one of", "one of", "at least one selected from", and "one selected from", when preceding a list of elements, modify the entire list of elements and do not modify the individual elements of the list. Further, the use of "may" when describing embodiments of the present disclosure refers to "one or more embodiments of the present disclosure".

In addition, as used herein, the terms "use", "using", and "used" may be considered synonymous with the terms "utilize", "utilizing", and "utilized", respectively.

As used herein, the terms "substantially", "about", and similar terms are used as terms of approximation and not as terms of degree, and are intended to account for the inherent deviations in measured or calculated values that would be recognized by those of ordinary skill in the art.

Also, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Although the example embodiments of the present disclosure have been described, it is understood that the present disclosure should not be limited to these example embodiments, but that various changes and modifications can be made by one ordinary skilled in the art within the spirit and scope of the present disclosure as recited in the claims and equivalents thereof.

What is claimed is:

1. A compound including nitrogen, represented by Formula 1:

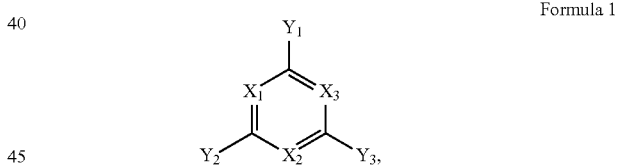

Formula 1 wherein in Formula 1, $X_1$ to $X_3$ are each independently CR or N, at least two of $X_1$ to $X_3$ are N, R is a hydrogen atom, a deuterium atom, or a substituted or unsubstituted alkyl group having 1 to 10 carbon atoms, $Y_1$ to $Y_3$ are each independently represented by one of Formulae 2 to 4, and at least two of $Y_1$ to $Y_3$ are represented by Formula 3 or 4:

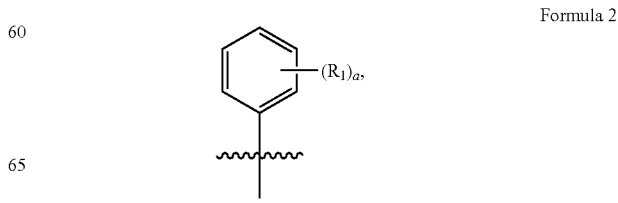

Formula 2

-continued

Formula 3

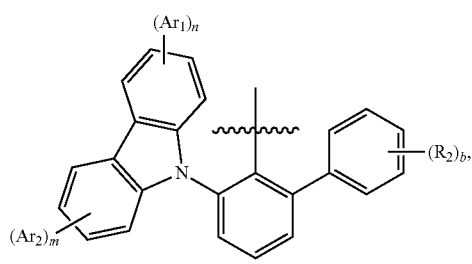

Formula 4

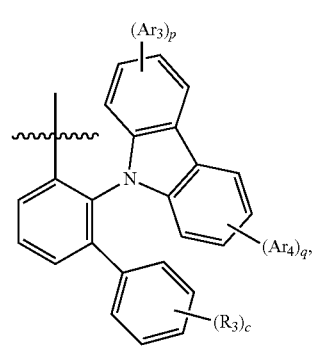

wherein in Formulae 2 to 4,

R$_1$ to R$_3$ are each independently a hydrogen atom, a deuterium atom, a halogen atom, a substituted or unsubstituted alkyl group having 1 to 10 carbon atoms, or a substituted or unsubstituted aryl group having 6 to 30 carbon atoms for forming a ring, Ar$_1$ to Ar$_4$ are each independently a hydrogen atom, a deuterium atom, a halogen atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring, a to c are each independently an integer of 0 to 5, and n, m, p, and q are each independently an integer of 0 to 4.

2. The compound including nitrogen of claim 1, wherein R$_1$ to R$_3$ are each independently a hydrogen atom, a deuterium atom, a fluorine atom, a substituted or unsubstituted alkyl group having 1 to 4 carbon atoms, a substituted or unsubstituted phenyl group, or a substituted or unsubstituted biphenyl group.

3. The compound including nitrogen of claim 1, wherein Ar$_1$ to Ar$_4$ are each independently a hydrogen atom, a deuterium atom, a fluorine atom, a substituted or unsubstituted alkyl group having 1 to 4 carbon atoms, a substituted or unsubstituted phenyl group, a substituted or unsubstituted biphenyl group, a substituted or unsubstituted carbazole group, a substituted or unsubstituted dibenzofuran group, or a substituted or unsubstituted dibenzothiophene group.

4. The compound including nitrogen of claim 1, wherein two of X$_1$ to X$_3$ are N, and the remaining one is CH.

5. The compound including nitrogen of claim 1, wherein X$_1$ to X$_3$ are N.

6. The compound including nitrogen of claim 1, wherein Y$_1$ to Y$_3$ are each independently represented by Formula 3 or 4.

7. The compound including nitrogen of claim 1, wherein the absolute value of a difference between a singlet energy level of the compound and a triplet energy level of the compound is about 0.2 eV or less.

8. The compound including nitrogen of claim 1, wherein the compound including nitrogen, represented by Formula 1 is one selected from compounds represented in Compound Group 1:

Compound Group 1

T-01

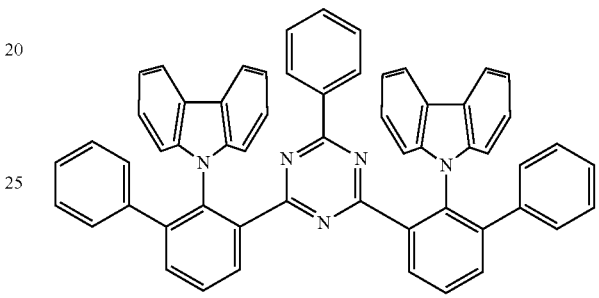

T-02

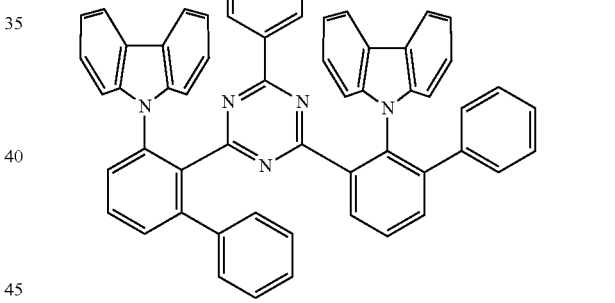

T-03

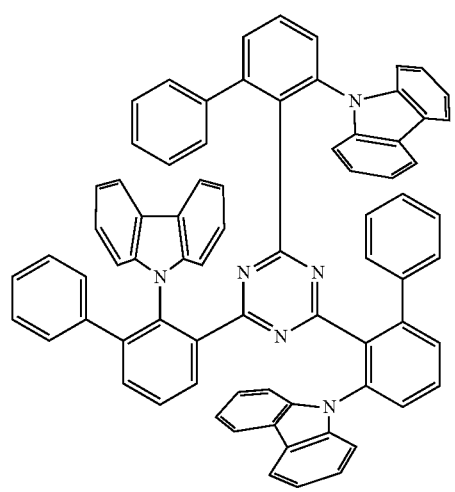

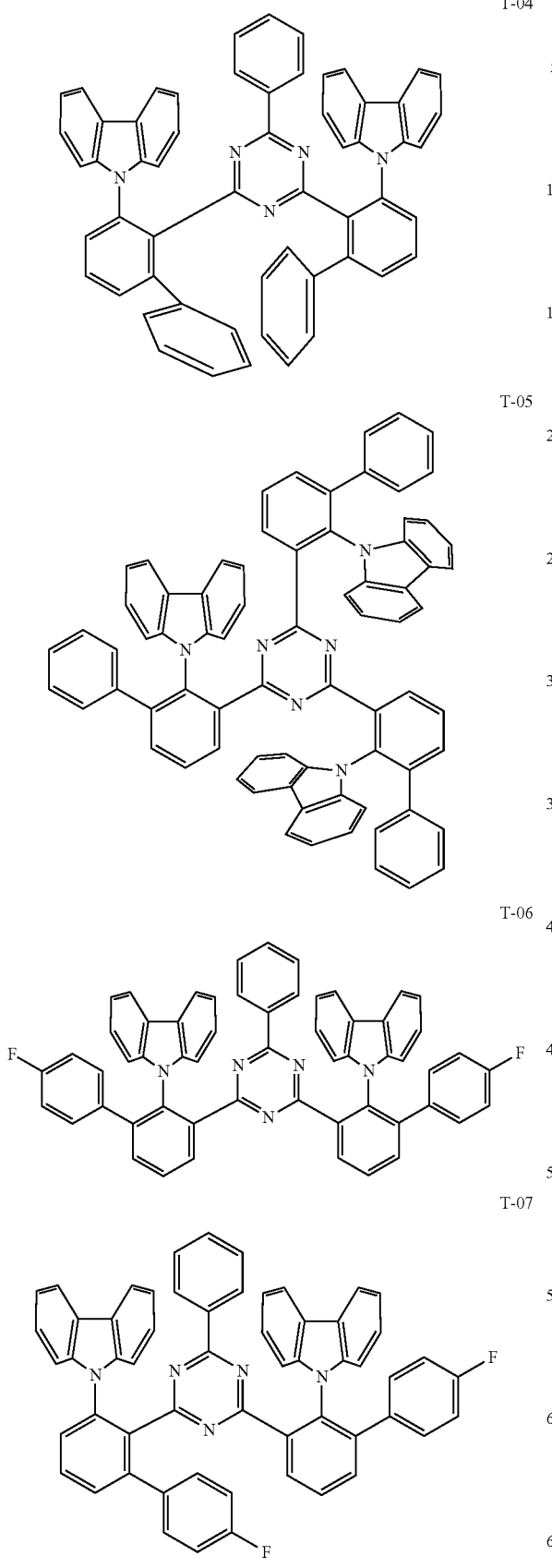
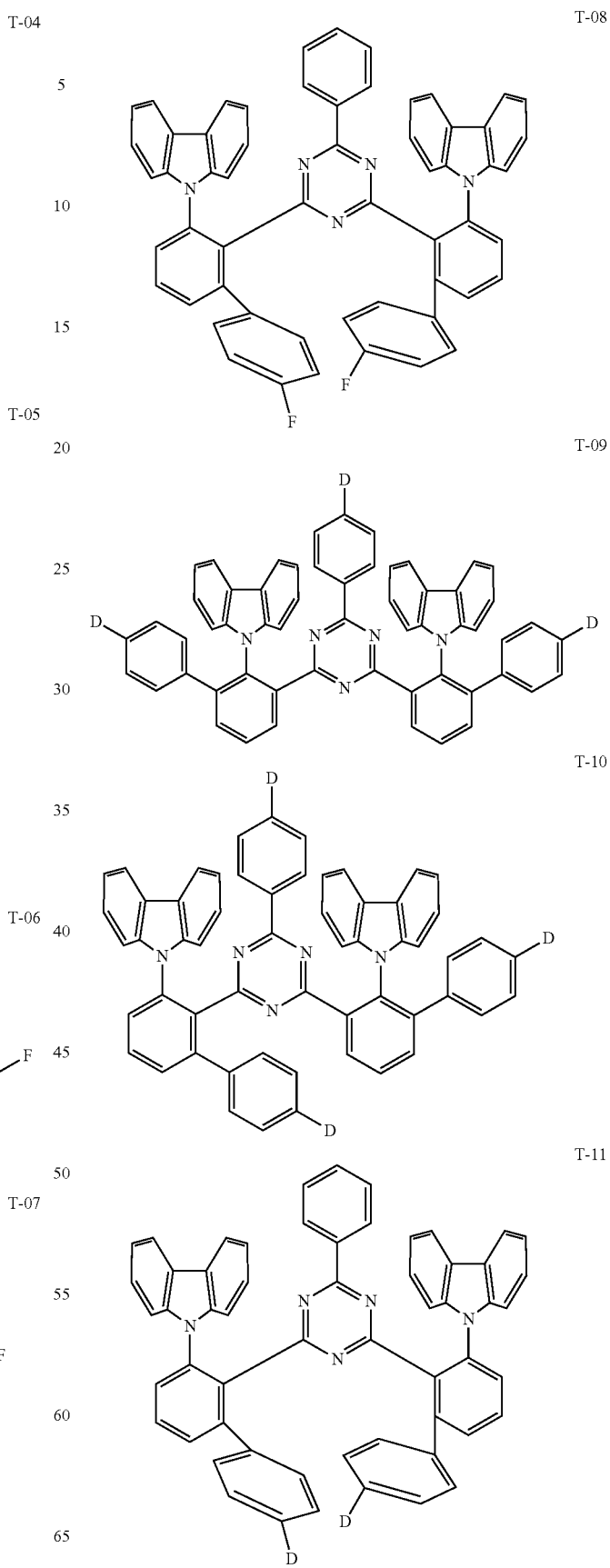

T-12
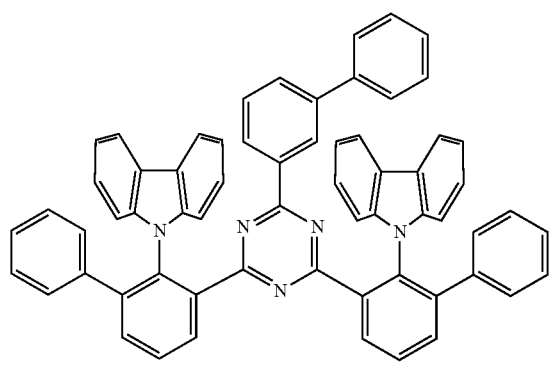
T-13
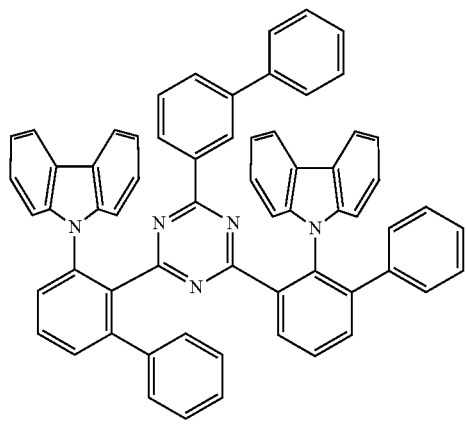
T-14
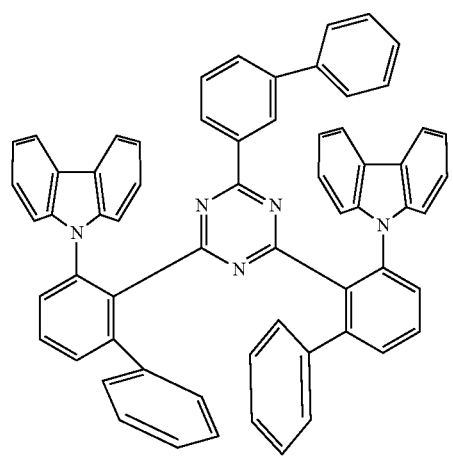
T-15
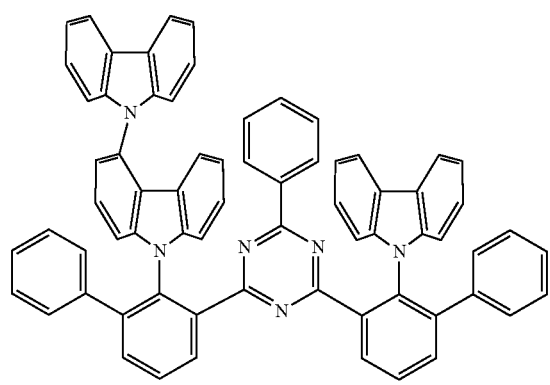
T-16
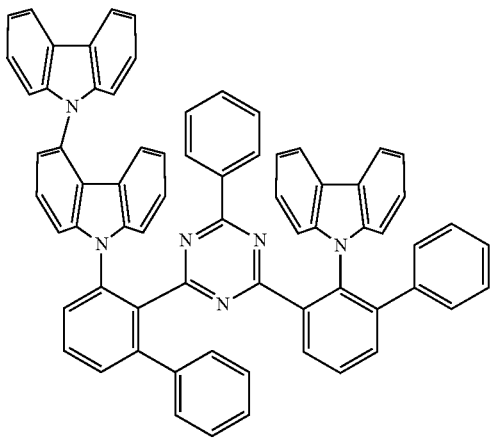
T-17
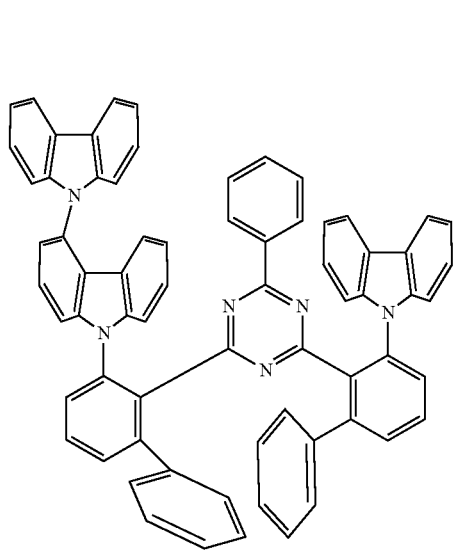
T-18
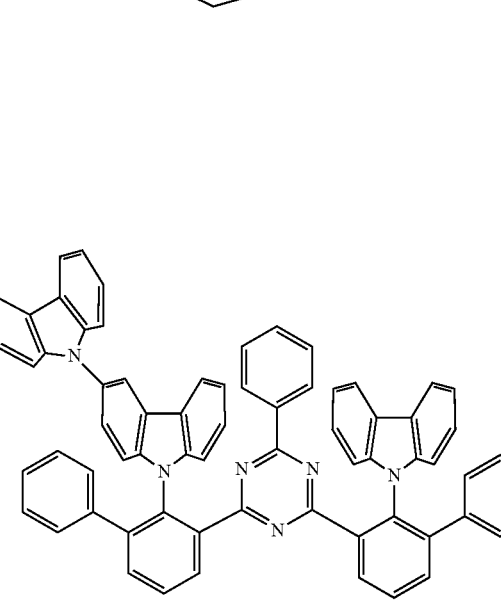

T-19
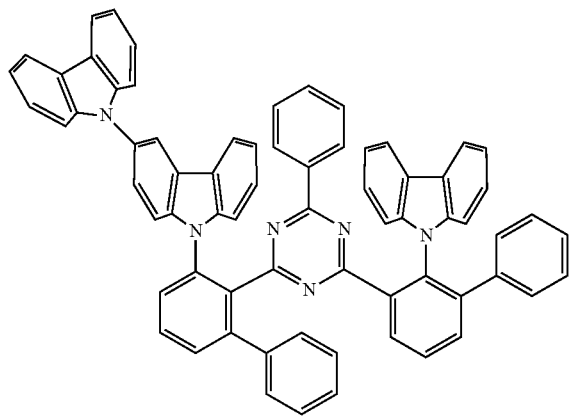
T-20
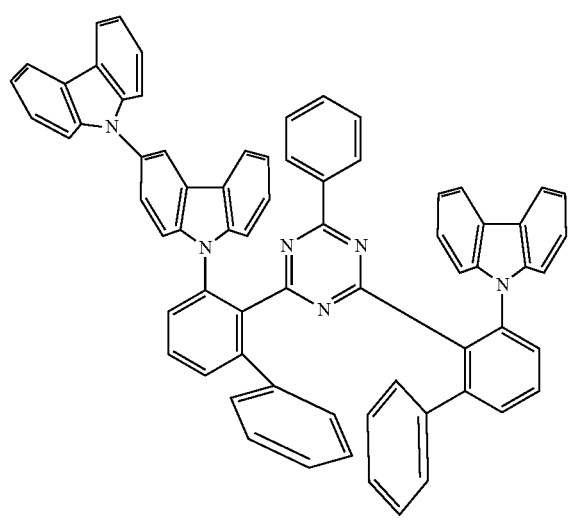
T-21
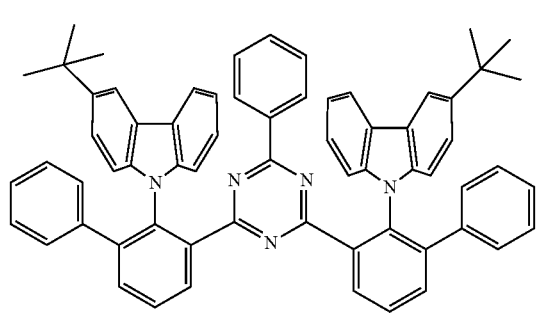
T-22
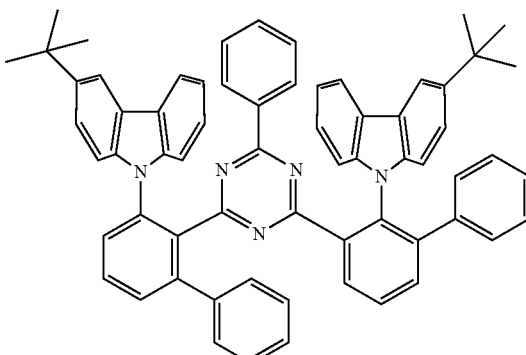
T-23
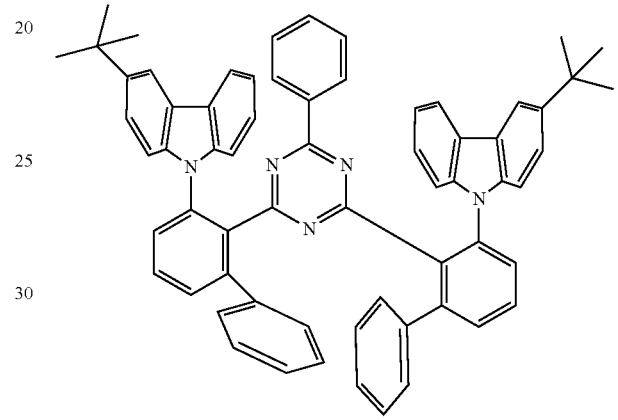
T-24
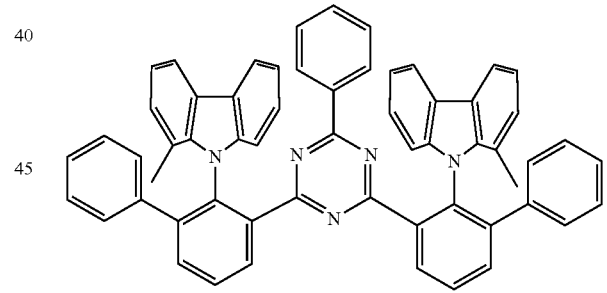
T-25
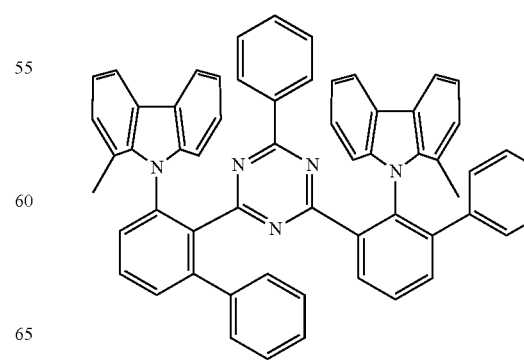

-continued
T-26
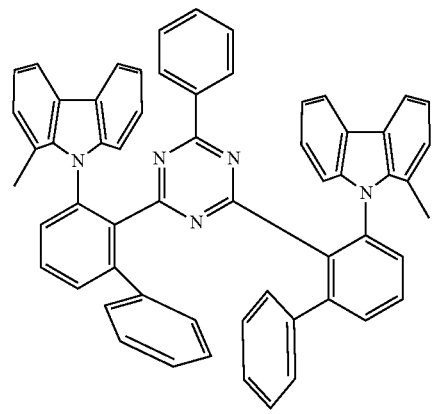
T-27
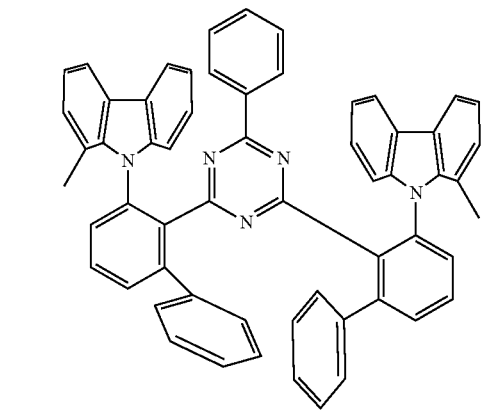
T-28
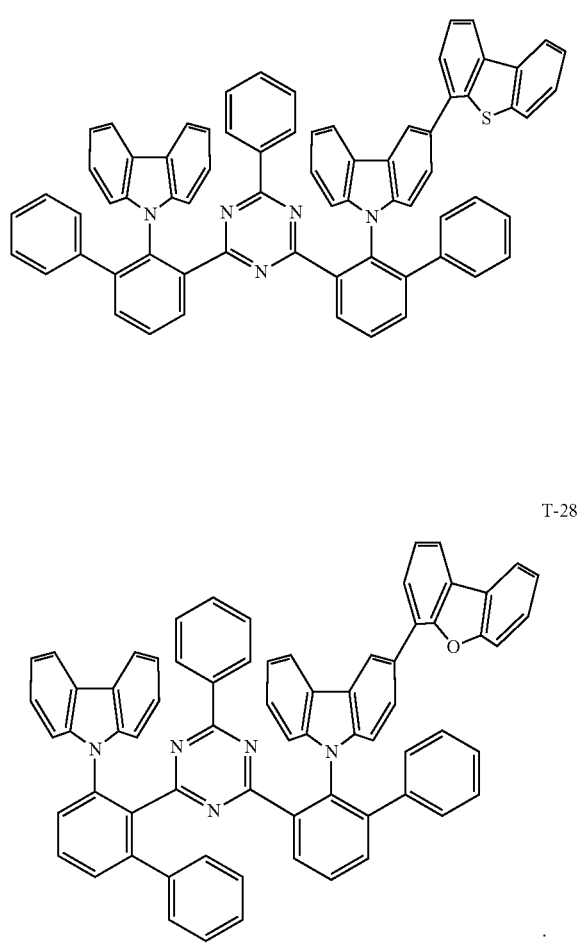
Compound Group 2
T-29
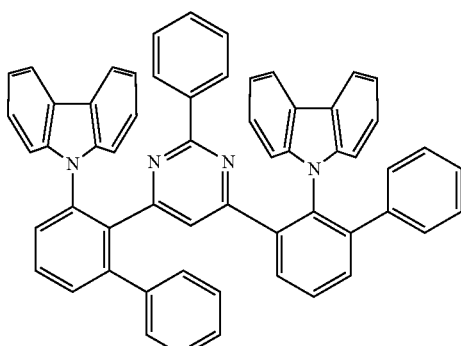
T-30
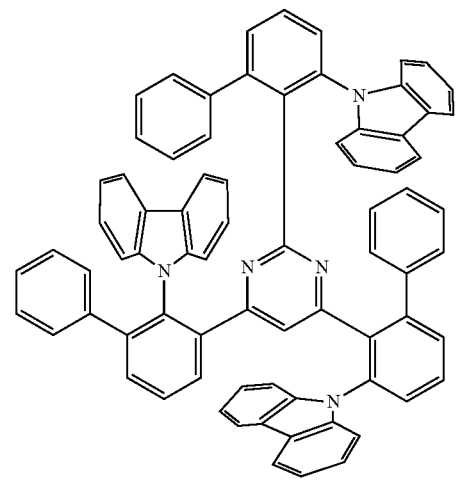
T-31
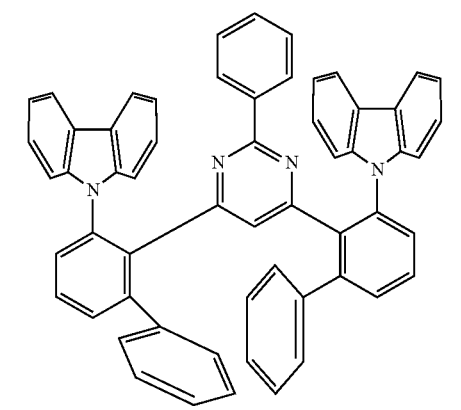
T-32
9. The compound including nitrogen of claim 1, wherein the compound including nitrogen represented by Formula 1 is one selected from compounds represented Compound Group 2:

T-33
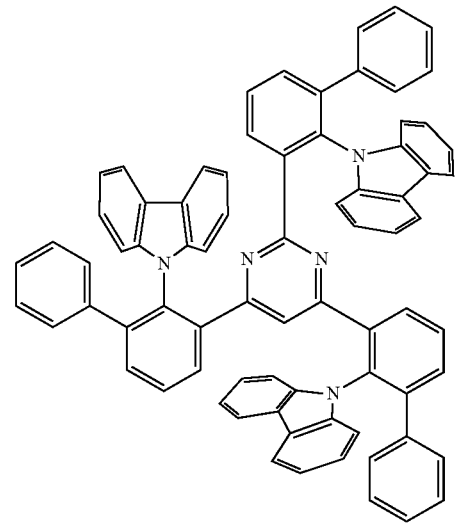
T-34
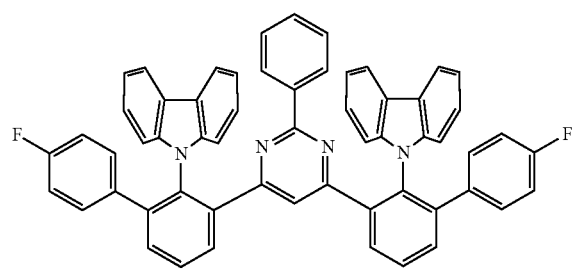
T-35
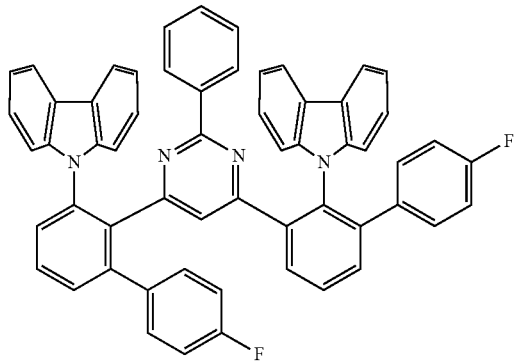
T-36
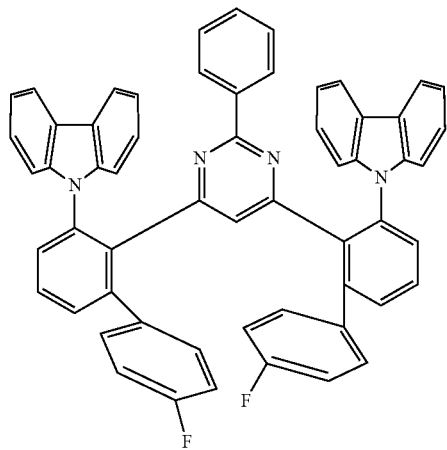
T-37
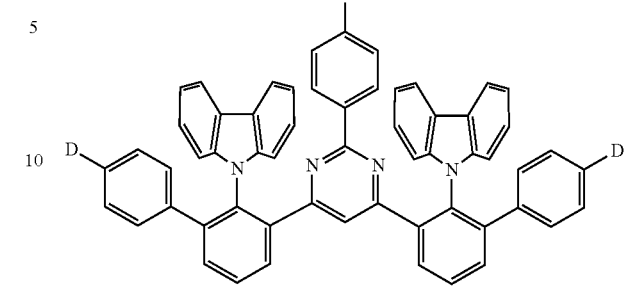
T-38
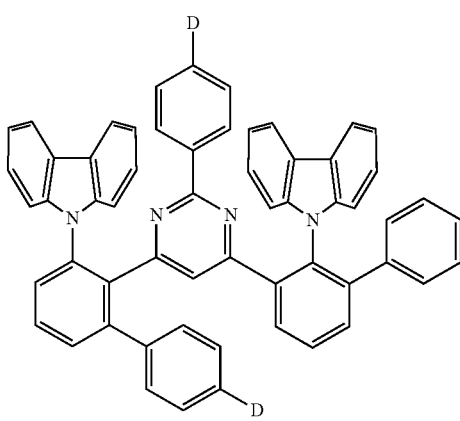
T-39
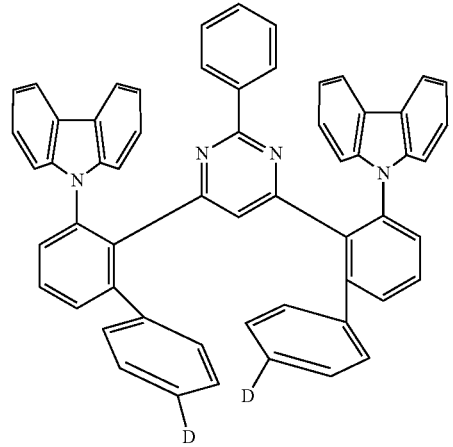
T-40
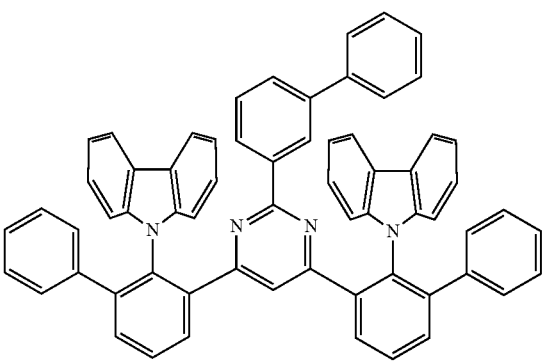

T-41
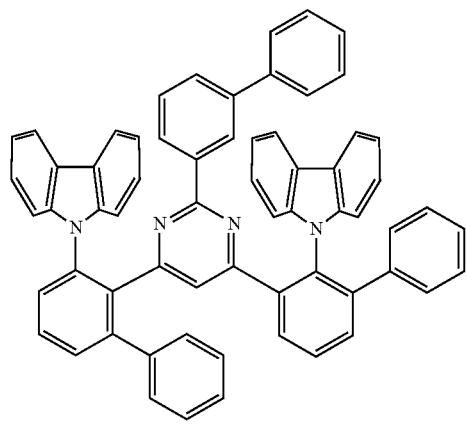
T-44
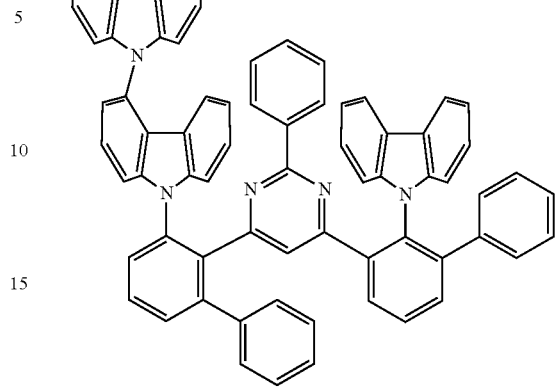
T-42
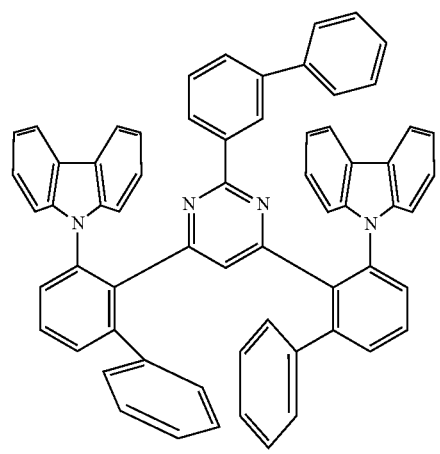
T-45
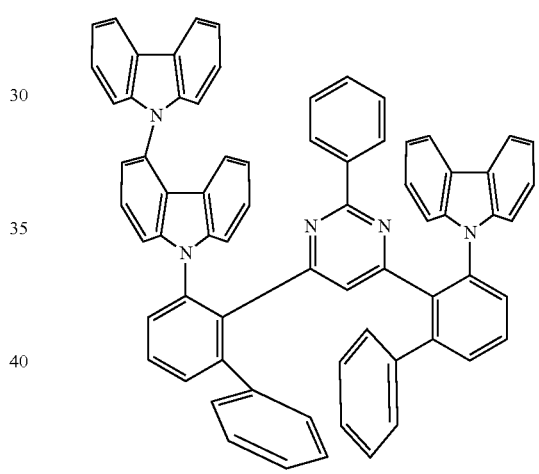
T-43
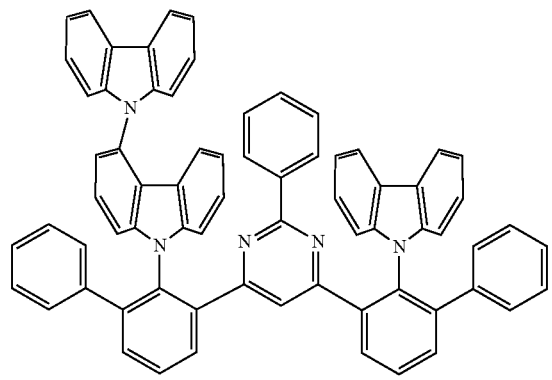
T-46
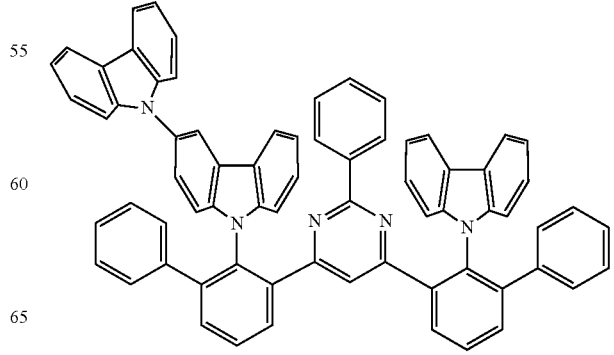

T-47
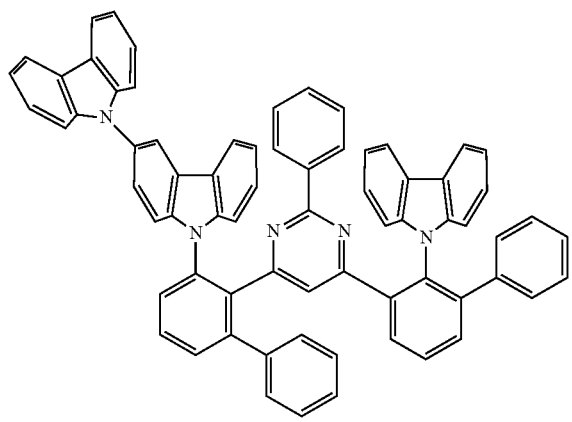
T-48
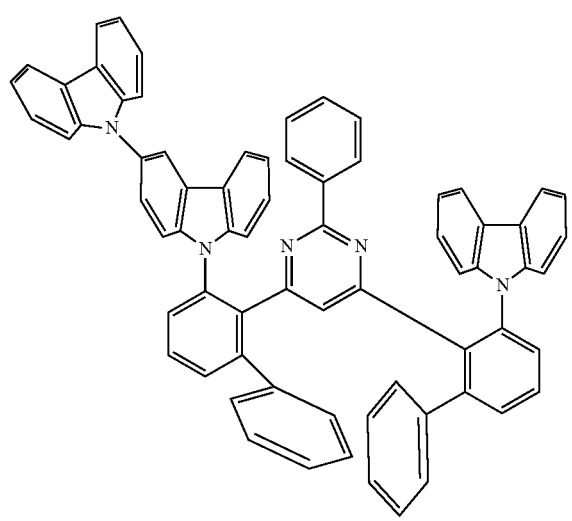
T-49
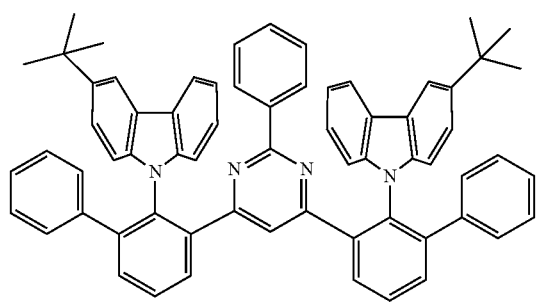
T-50
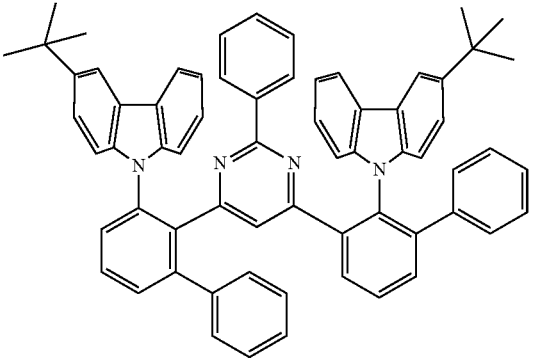
T-51
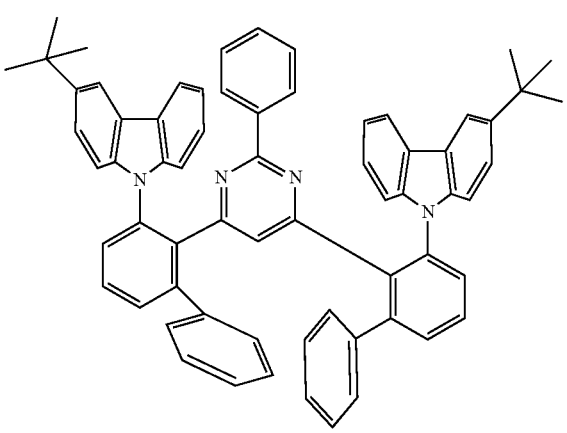
T-52
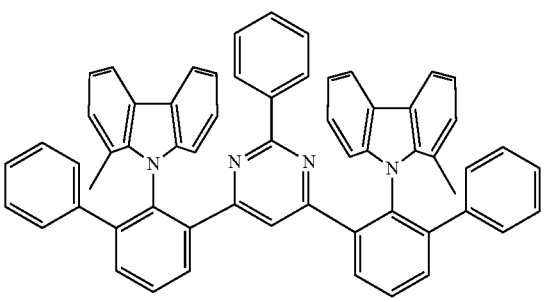
T-53
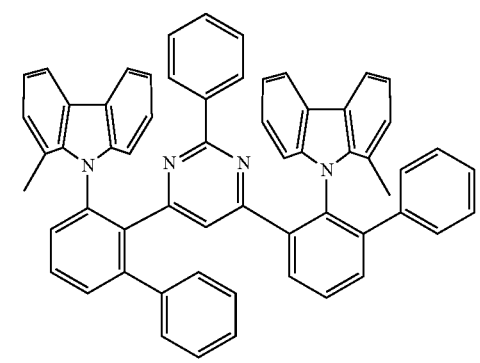

-continued

T-54

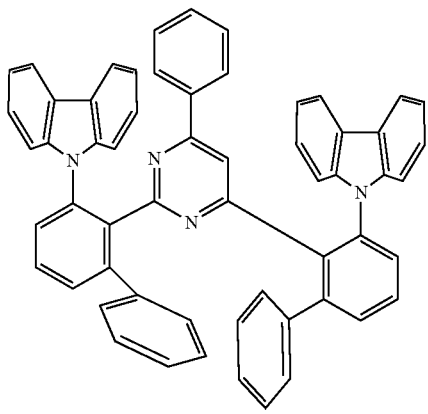

T-55

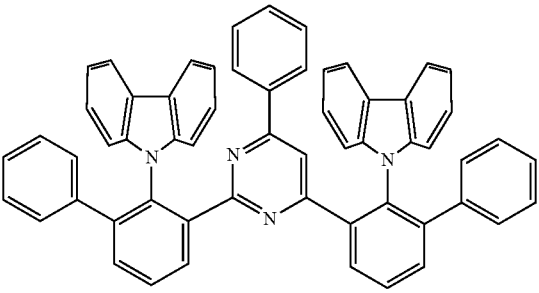

T-56

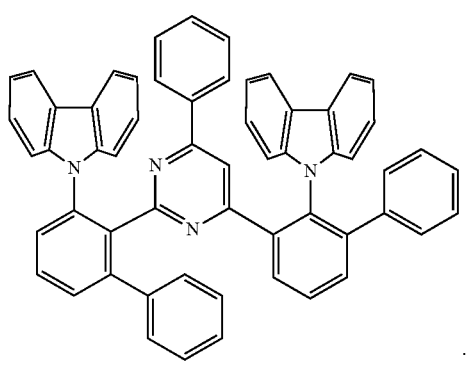

10. An organic electroluminescence device, comprising:
a first electrode;
a hole transport region on the first electrode;
an emission layer on the hole transport region;
an electron transport region on the emission layer; and
a second electrode on the electron transport region,
wherein the first electrode and the second electrode each independently comprise at least one selected from Ag, Mg, Cu, Al, Pt, Pd, Au, Ni, Nd, Ir, Cr, Li, Ca, LiF/Ca, LiF/Al, Mo, Ti, In, Sn, and Zn, a compound of two or more thereof, a mixture of two or more thereof, or an oxide thereof, wherein the emission layer comprises a compound including nitrogen represented by Formula 1:

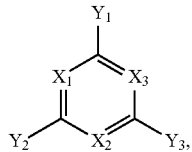

Formula 1 wherein in Formula 1,
$X_1$ to $X_3$ are each independently CR or N,
at least two of $X_1$ to $X_3$ are N,
R is a hydrogen atom, a deuterium atom, or a substituted or unsubstituted alkyl group having 1 to 10 carbon atoms,
$Y_1$ to $Y_3$ are each independently represented by one of Formulae 2 to 4, and
at least two of $Y_1$ to $Y_3$ are represented by Formula 3 or 4:

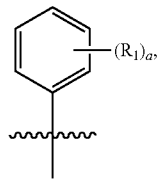

Formula 2

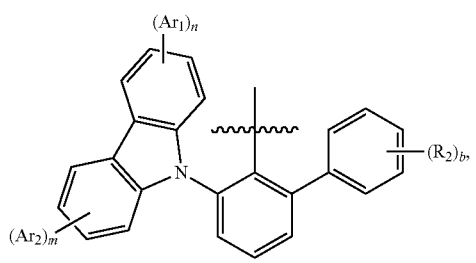

Formula 3

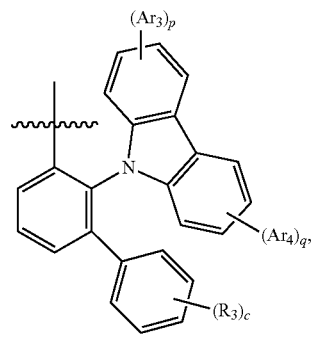

Formula 4 wherein in Formulae 2 to 4,
$R_1$ to $R_3$ are each independently a hydrogen atom, a deuterium atom, a halogen atom, a substituted or unsubstituted alkyl group having 1 to 10 carbon atoms, or a substituted or unsubstituted aryl group having 6 to 30 carbon atoms for forming a ring,
$Ar_1$ to $Ar_4$ are each independently a hydrogen atom, a deuterium atom, a halogen atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring, a to c are each independently an integer of 0 to 5, and n, m, p, and q are each independently an integer of 0 to 4.

11. The organic electroluminescence device of claim 10, wherein:
the emission layer comprises a host and a dopant, and
the dopant comprises the compound including nitrogen, represented by Formula 1.

12. The organic electroluminescence device of claim 11, wherein the dopant comprises a first dopant and a second dopant, and
the first dopant or the second dopant comprises the compound including nitrogen represented by Formula 1.

13. The organic electroluminescence device of claim 10, wherein the emission layer is to emit thermally activated delayed fluorescence.

14. The organic electroluminescence device of claim 10, wherein $R_1$ to $R_3$ are each independently a hydrogen atom, a deuterium atom, a fluorine atom, a substituted or unsubstituted alkyl group having 1 to 4 carbon atoms, a substituted or unsubstituted phenyl group, or a substituted or unsubstituted biphenyl group.

15. The organic electroluminescence device of claim 10, wherein $Ar_1$ to $Ar_4$ are each independently a hydrogen atom, a deuterium atom, a fluorine atom, a substituted or unsubstituted alkyl group having 1 to 4 carbon atoms, a substituted or unsubstituted phenyl group, a substituted or unsubstituted biphenyl group, a substituted or unsubstituted carbazole group, a substituted or unsubstituted dibenzofuran group, or a substituted or unsubstituted dibenzothiophene group.

16. The organic electroluminescence device of claim 10, wherein two of $X_1$ to $X_3$ are N, and the remaining one is CH.

17. The organic electroluminescence device of claim 10, wherein $X_1$ to $X_3$ are N.

18. The organic electroluminescence device of claim 10, wherein $Y_1$ to $Y_3$ are each independently represented by Formula 3 or 4.

19. The organic electroluminescence device of claim 10, wherein the compound including nitrogen, represented by Formula 1 is at least one selected from compounds represented in Compound Group 1:

Compound Group 1

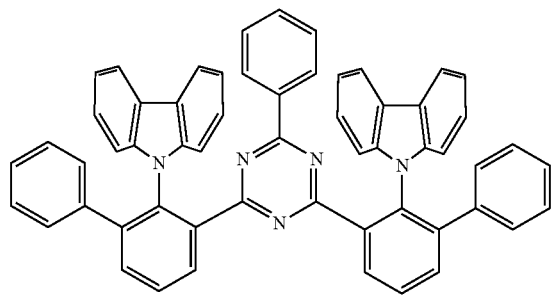

T-01

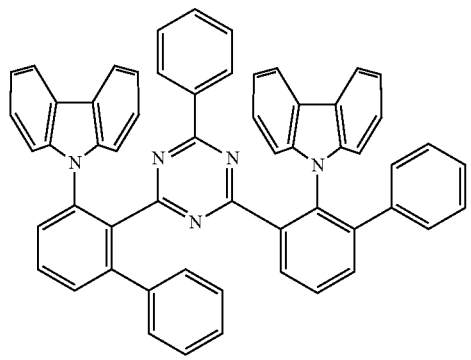

T-02

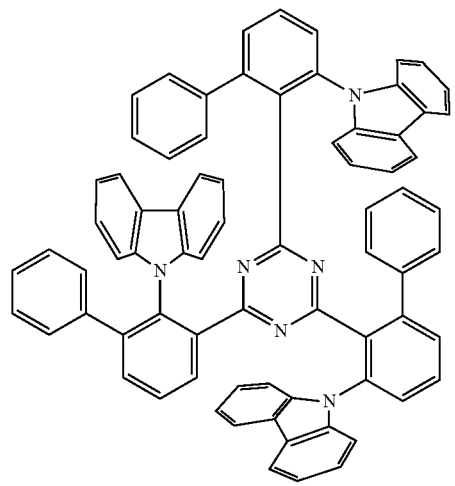

T-03

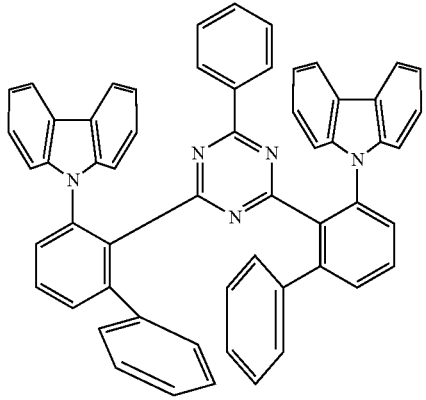

T-04

-continued
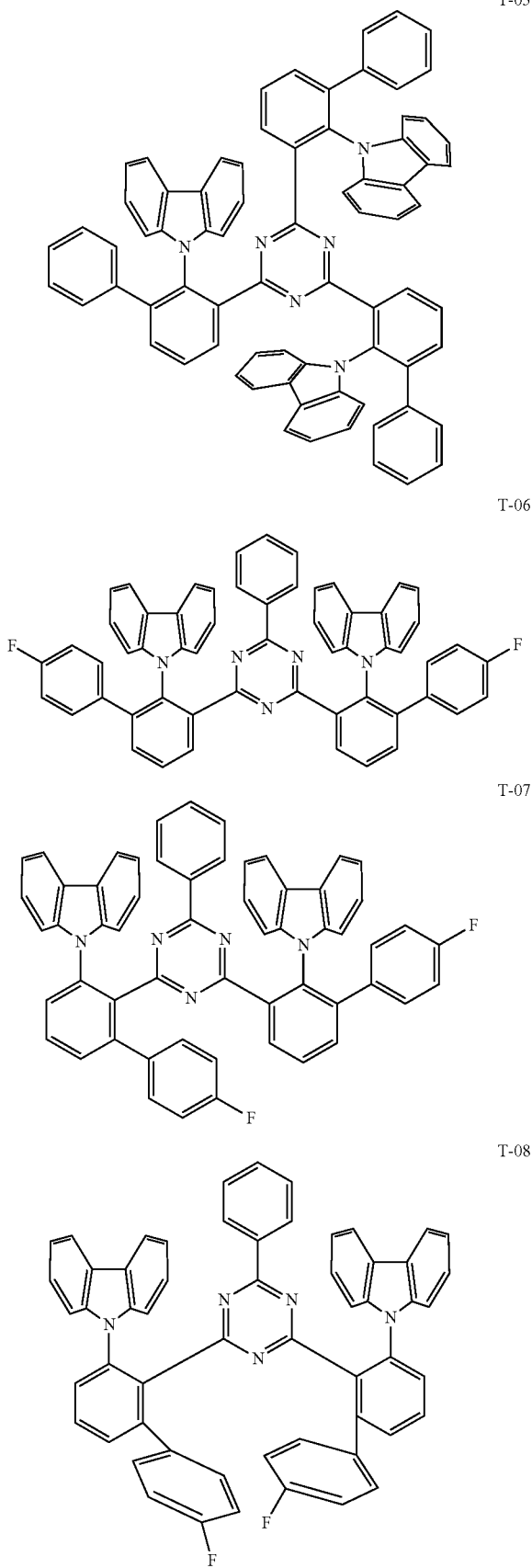
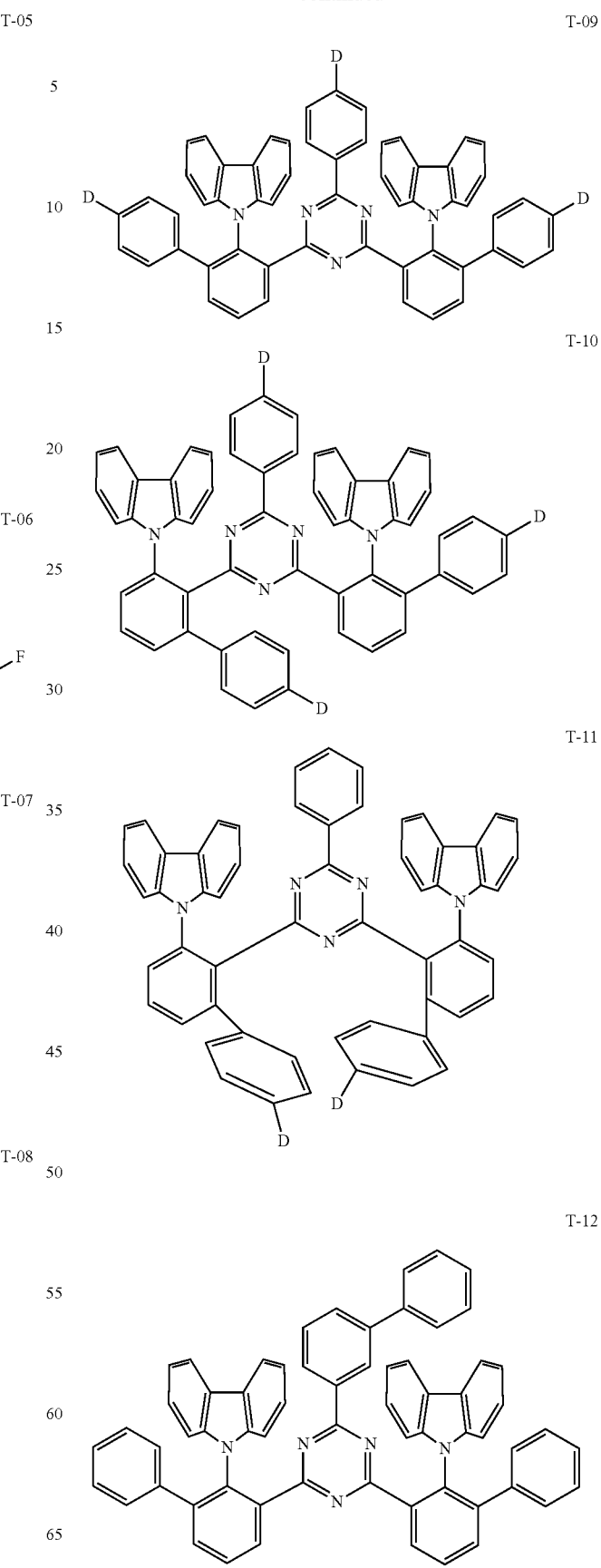

T-13
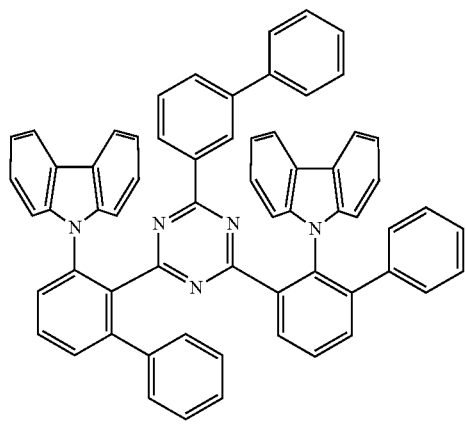
T-16
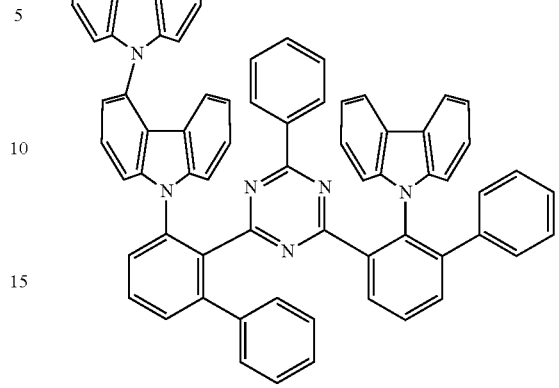
T-14
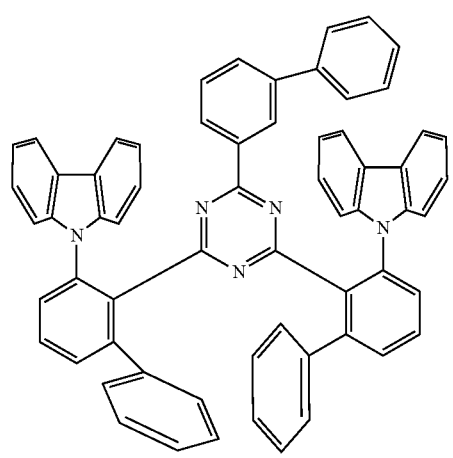
T-17
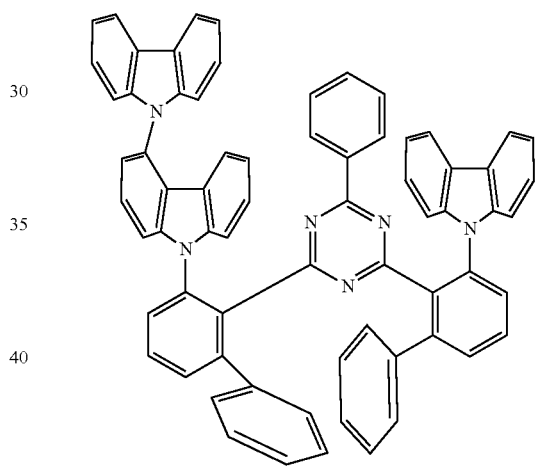
T-15
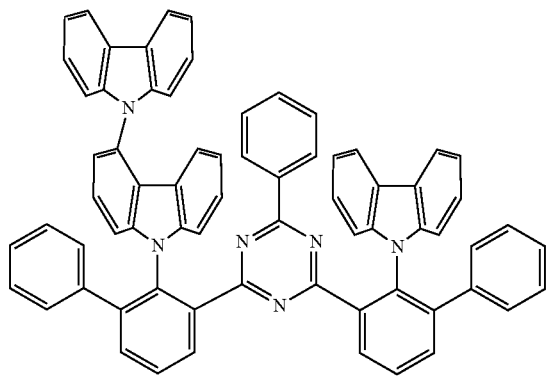
T-18

T-19
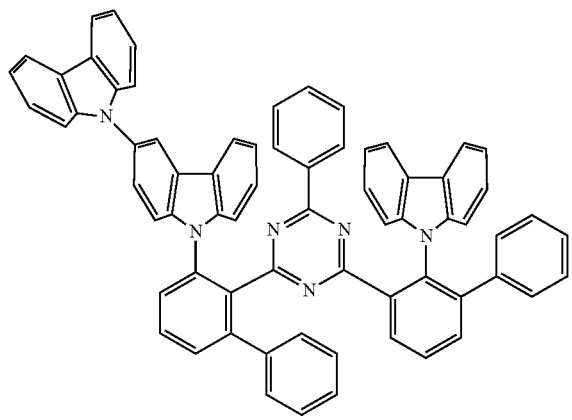
T-20
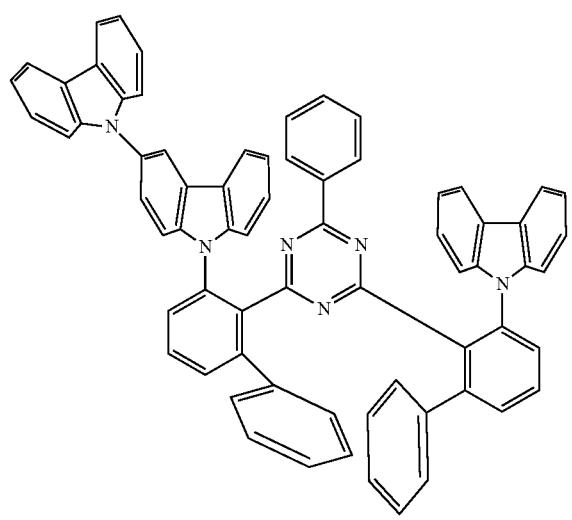
T-21
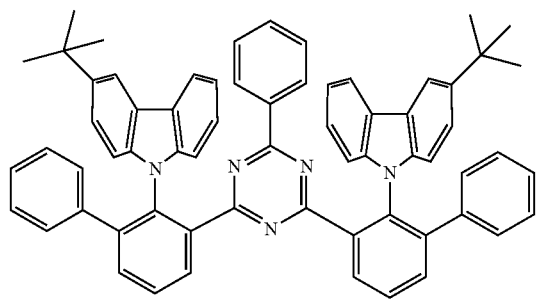
T-22
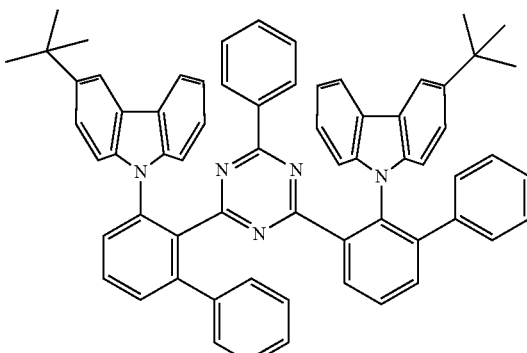
T-23
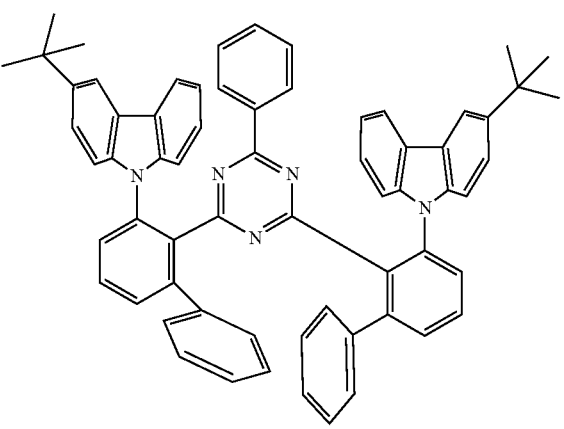
T-24
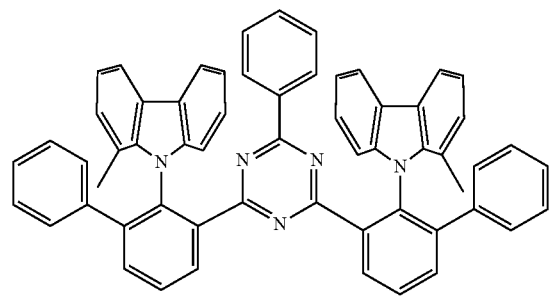
T-25
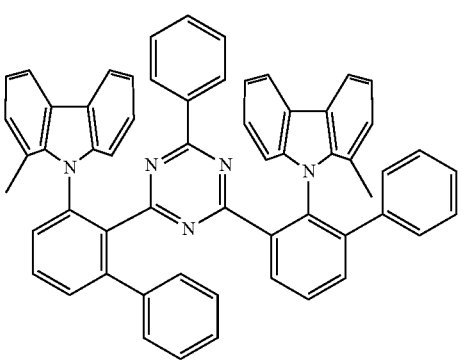

-continued
Compound Group 2
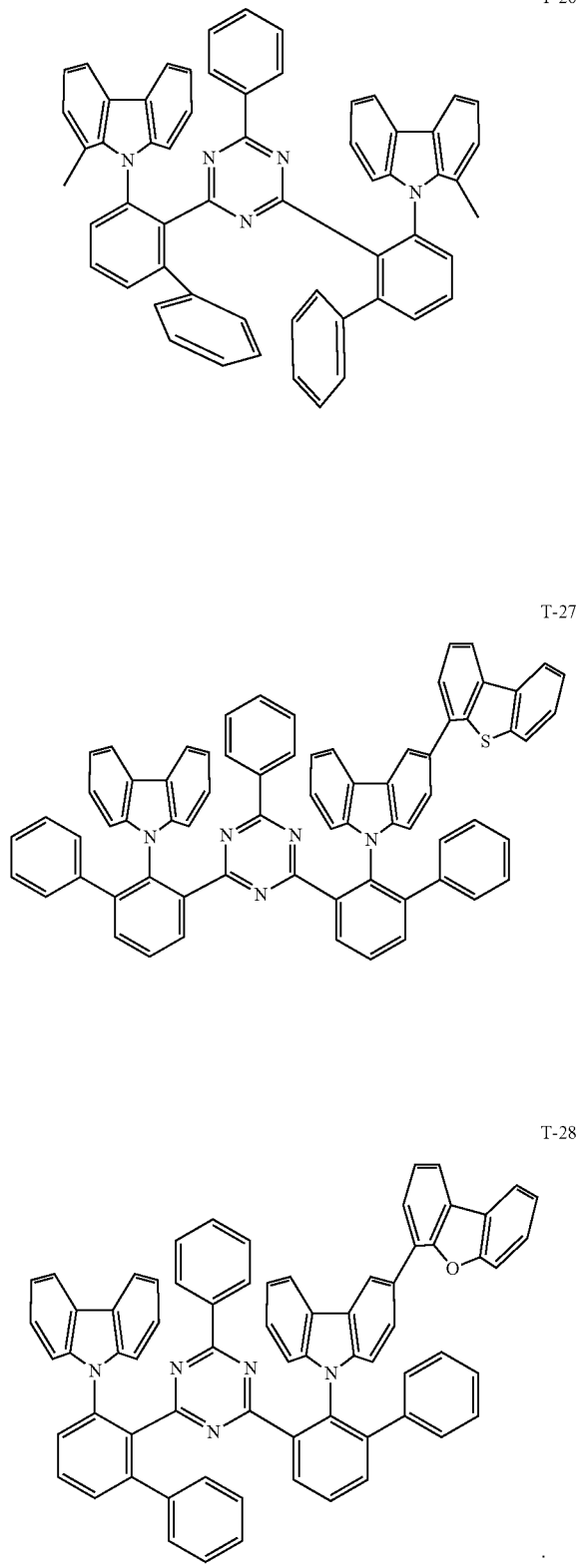
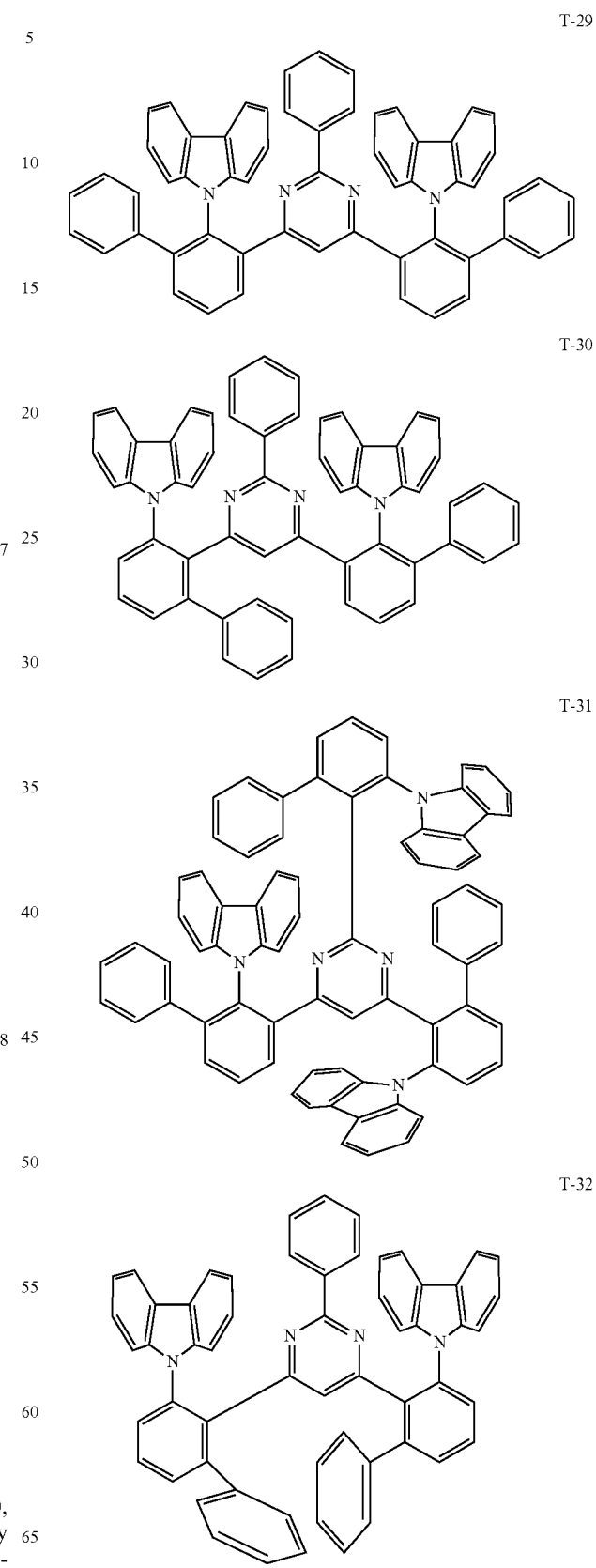
20. The organic electroluminescence device of claim 10, wherein the compound including nitrogen, represented by Formula 1 is at least one selected from compounds represented in Compound Group 2:

T-33
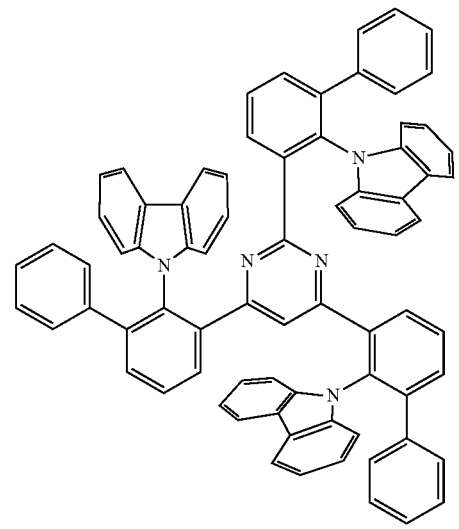
T-34
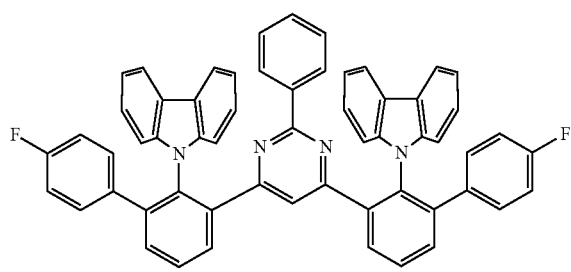
T-35
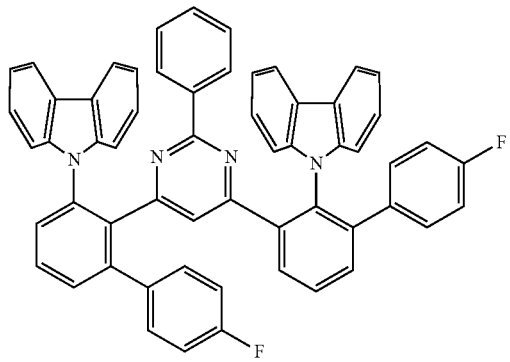
T-36
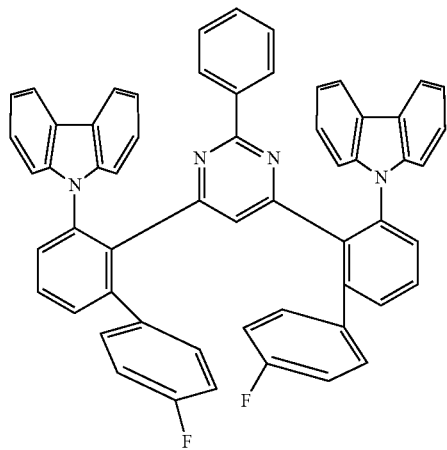
T-37
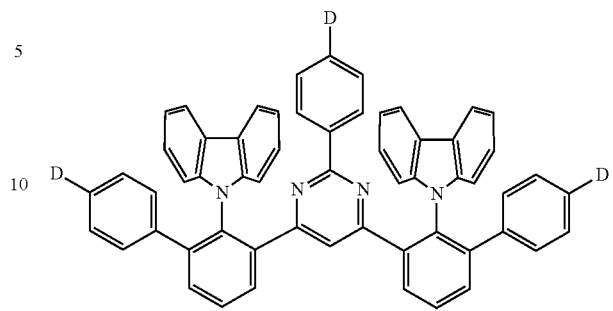
T-38
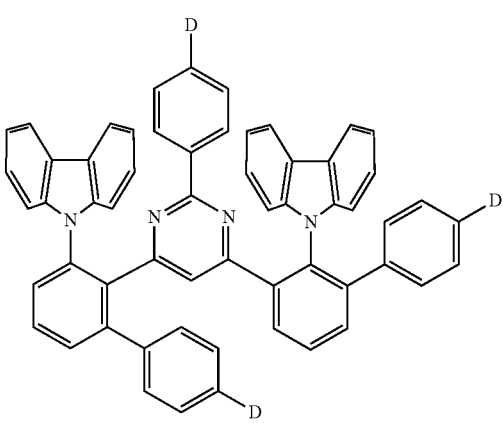
T-39
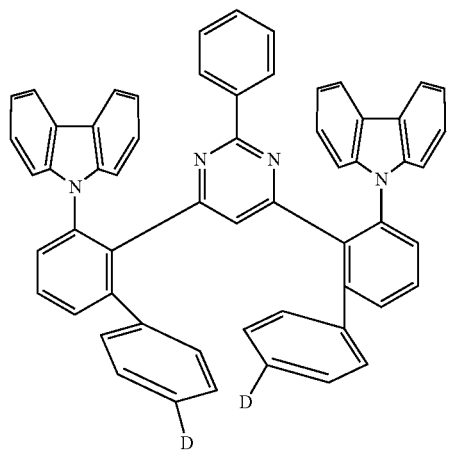
T-40
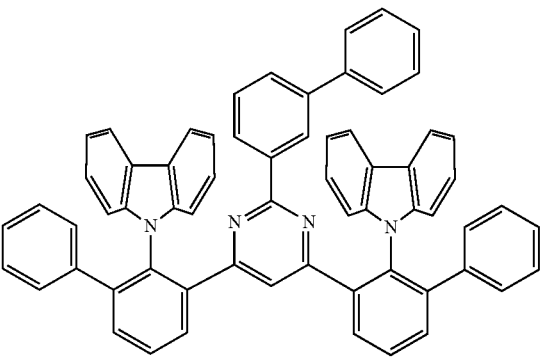

T-41
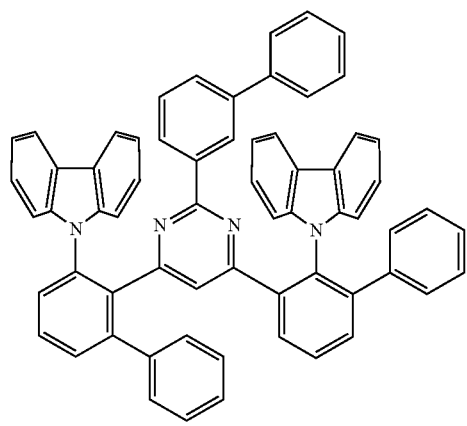
T-42
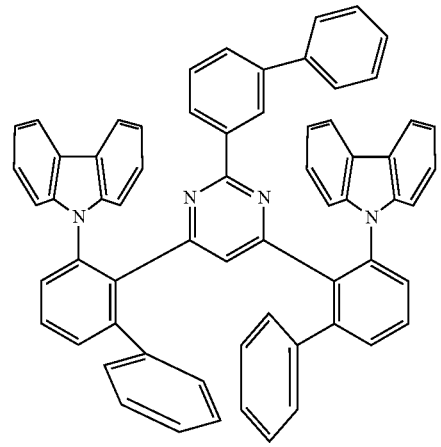
T-43
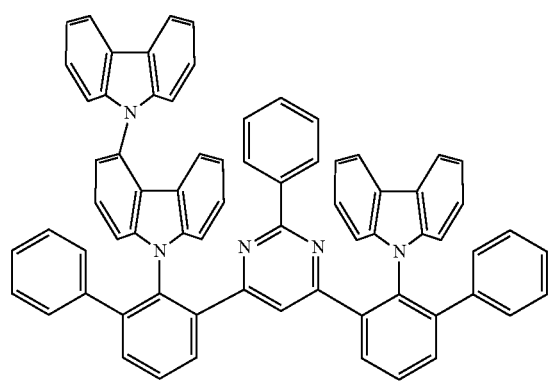
T-44
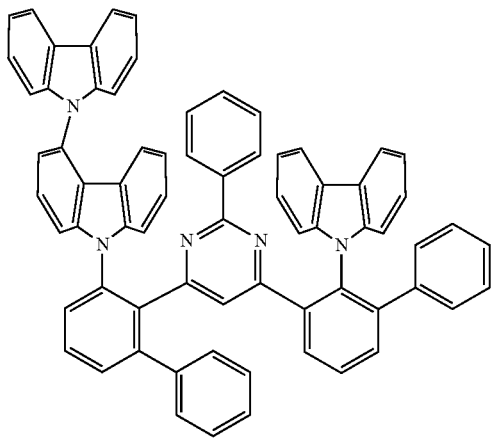
T-45
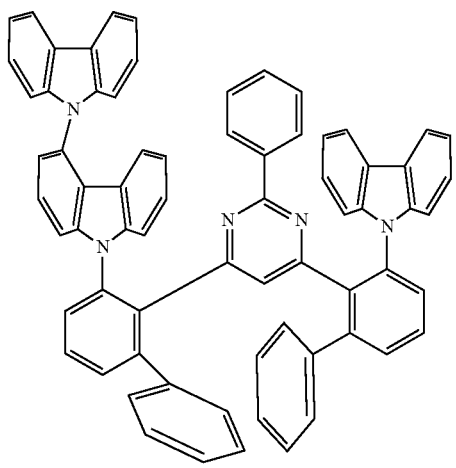
T-46
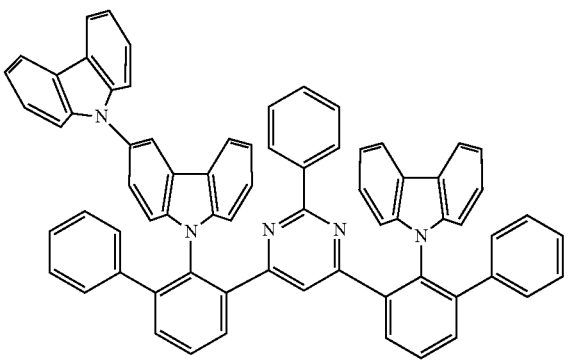

-continued
T-47
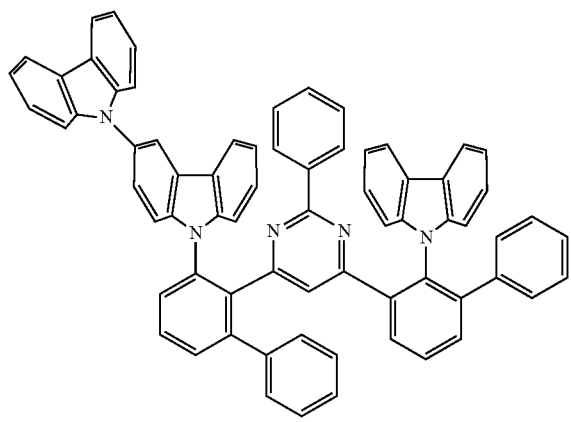
T-48
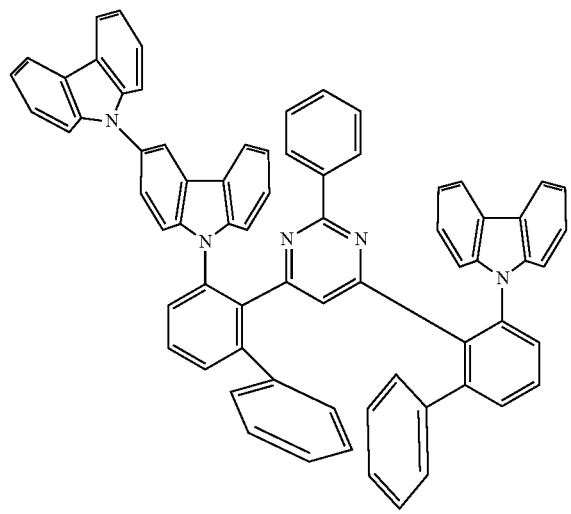
T-49
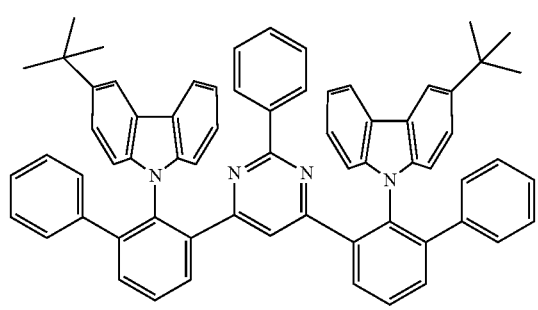
-continued
T-50
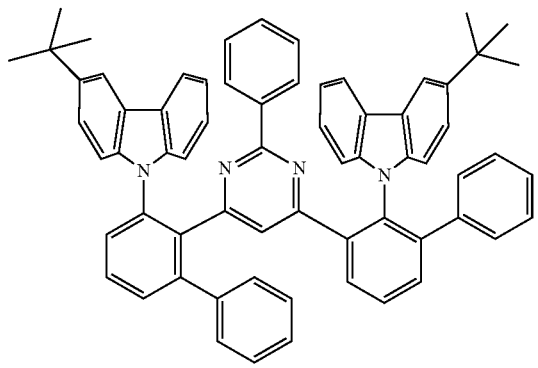
T-51
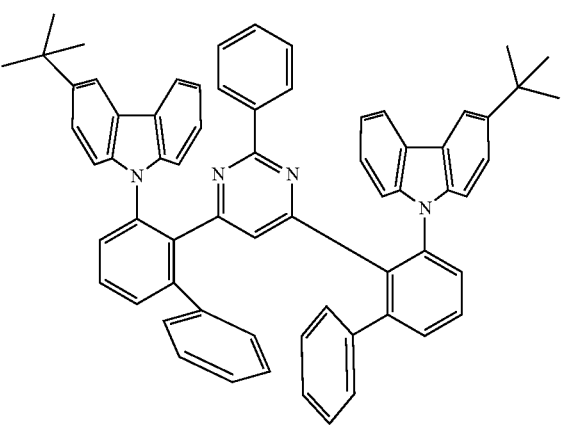
T-52
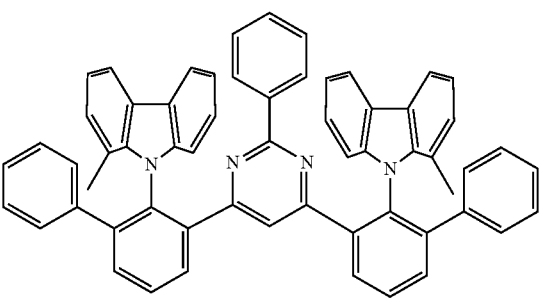

-continued
T-53
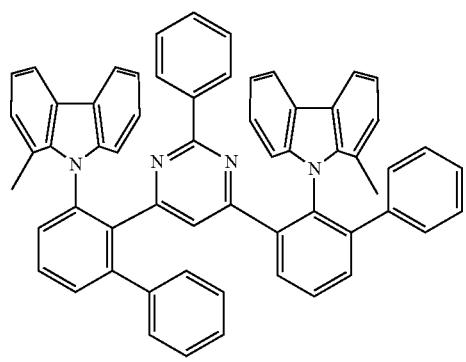
T-55
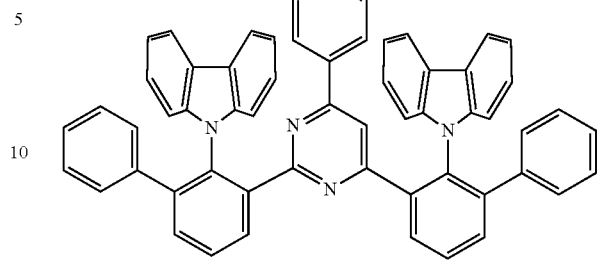
T-54
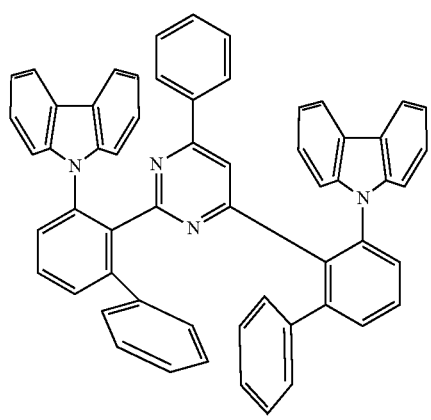
T-56
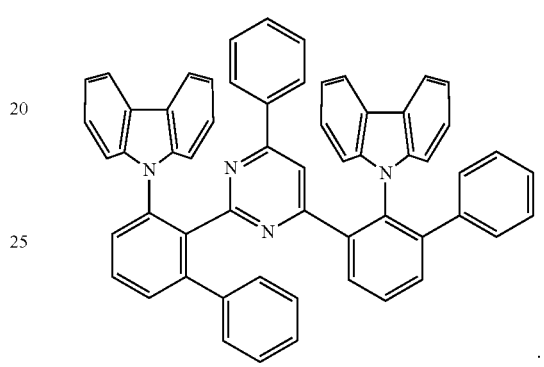
* * * * *